US010245775B2

(12) United States Patent
Geshlider et al.

(10) Patent No.: US 10,245,775 B2
(45) Date of Patent: Apr. 2, 2019

(54) METHOD AND APPARATUS FOR TRANSFERRING A DIGITAL PROFILE OF A RESIDUAL LIMB TO A PROSTHETIC SOCKET STRUT

(71) Applicant: LIM INNOVATIONS, INC., San Francisco, CA (US)

(72) Inventors: Robert Adam Geshlider, San Francisco, CA (US); Fred S. Williams, San Francisco, CA (US); Jesse Robert Williams, San Francisco, CA (US); Garrett Ray Hurley, San Francisco, CA (US); Andrew C. Pedtke, San Francisco, CA (US)

(73) Assignee: LIM Innovations, Inc., San Francisco, CA (US)

( * ) Notice: Subject to any disclaimer, the term of this patent is extended or adjusted under 35 U.S.C. 154(b) by 621 days.

(21) Appl. No.: 14/731,163

(22) Filed: Jun. 4, 2015

(65) Prior Publication Data
US 2015/0352775 A1 Dec. 10, 2015

Related U.S. Application Data

(60) Provisional application No. 62/007,742, filed on Jun. 4, 2014, provisional application No. 62/045,433, filed (Continued)

(51) Int. Cl.
*B29C 51/18* (2006.01)
*B29C 51/12* (2006.01)
(Continued)

(52) U.S. Cl.
CPC ............. *B29C 51/18* (2013.01); *B29C 51/12* (2013.01); *B29C 51/30* (2013.01); *B29C 51/46* (2013.01); *A61F 2240/004* (2013.01)

(58) Field of Classification Search
CPC ..................... A61F 2002/5053; A61F 2/5046
(Continued)

(56) References Cited

U.S. PATENT DOCUMENTS

| 1,144,681 A | 6/1915 | Apgar |
| 1,482,185 A * | 1/1924 | Egerton ................. B32B 27/00 |
| | | 156/154 |

(Continued)

FOREIGN PATENT DOCUMENTS

| DE | 319623 | 3/1920 |
| EP | 204407 | 12/1986 |

(Continued)

OTHER PUBLICATIONS

Quigley, Michael. Prosthetic Management: Overview, Methods and Materials. Chapter 4. Atlas of Limb Prosthetics: Surgical, Prosthetic, and Rehabilitation Principles. (Second Edition) 1992.
(Continued)

*Primary Examiner* — Cachet I Sellman
(74) *Attorney, Agent, or Firm* — Gordon & Jacobson, P.C.

(57) ABSTRACT

Embodiments of the provided technology relate to methods, devices, and systems that drive a transfer of the digital profile of residual limb contours to a thermoplastic article such as a prosthetic socket strut. A method of reforming a thermoplastic article to assume a desired shape, such as a contour that replicates or is complementary to the contour of a body portion, may include heating a thermoplastic article to render the article malleable. The method may further include placing the thermoplastic article against a molding surface having a desired shape that replicates the portion of the body part. Next, the thermoplastic article may be pressed against the molding surface with a compliant molding press to reform at least a portion of the article into the desired
(Continued)

shape. The reformed thermoplastic article may then be removed from the molding surface, the article retaining the desired shape after removal.

18 Claims, 39 Drawing Sheets

Related U.S. Application Data on Sep. 3, 2014, provisional application No. 62/128,218, filed on Mar. 4, 2015.

(51) Int. Cl.
  *B29C 51/46* (2006.01)
  *B29C 51/30* (2006.01)
(58) Field of Classification Search
  USPC .................................................. 264/222
  See application file for complete search history.

(56) References Cited

U.S. PATENT DOCUMENTS

| | | | |
|---|---|---|---|
| 1,893,853 A | 1/1933 | Tullis | |
| 2,025,835 A | 12/1935 | Trautman | |
| 2,229,728 A | 1/1941 | Eddels | |
| 2,410,888 A * | 11/1946 | Lucy | B28B 7/02 |
| | | | 249/155 |
| 2,634,424 A | 4/1953 | O'Gorman | |
| 2,671,225 A * | 3/1954 | Schoene | A61F 2/80 |
| | | | 623/36 |
| 2,759,271 A | 8/1956 | Von Duyke | |
| 2,804,653 A * | 9/1957 | Talalay | B29C 44/3415 |
| | | | 264/28 |
| 2,908,016 A | 10/1959 | Botko | |
| 2,949,674 A | 8/1960 | Wexler | |
| 3,186,006 A | 6/1965 | Miller | |
| 3,678,587 A | 7/1972 | Madden | |
| 4,161,042 A * | 7/1979 | Cottingham | A61F 2/60 |
| | | | 623/33 |
| 4,225,982 A | 10/1980 | Cochrane et al. | |
| 4,300,245 A | 11/1981 | Saunders | |
| 4,459,709 A | 7/1984 | Leal et al. | |
| 4,704,129 A | 11/1987 | Massey | |
| 4,715,124 A | 12/1987 | Harrington | |
| 4,783,293 A | 11/1988 | Wellershaus et al. | |
| 4,842,608 A | 6/1989 | Marx et al. | |
| 4,872,879 A | 10/1989 | Shamp | |
| 4,921,502 A | 5/1990 | Shamp | |
| 4,988,360 A | 1/1991 | Shamp | |
| 5,003,969 A | 4/1991 | Azer et al. | |
| 5,014,441 A | 5/1991 | Pratt | |
| 5,108,456 A | 4/1992 | Coonan, III | |
| 5,116,382 A | 5/1992 | Steinkamp et al. | |
| 5,133,777 A | 7/1992 | Arbogast et al. | |
| 5,168,635 A | 12/1992 | Hoffman | |
| 5,201,773 A | 4/1993 | Carideo, Jr. | |
| 5,201,775 A * | 4/1993 | Arbogast | A61F 2/60 |
| | | | 264/275 |
| 5,246,464 A | 9/1993 | Sabolich | |
| 5,312,669 A | 5/1994 | Bedard | |
| 5,376,129 A * | 12/1994 | Faulkner | A61F 2/5046 |
| | | | 623/31 |
| 5,387,245 A | 2/1995 | Fay et al. | |
| 5,431,624 A | 7/1995 | Saxton et al. | |
| 5,445,770 A * | 8/1995 | Adam | A61C 7/12 |
| | | | 264/16 |
| 5,500,067 A * | 3/1996 | Jenkner | A43B 13/187 |
| | | | 156/145 |
| 5,503,543 A * | 4/1996 | Laghi | A61F 2/5046 |
| | | | 264/222 |
| 5,520,529 A | 5/1996 | Heckel | |
| 5,529,575 A | 6/1996 | Klotz | |
| 5,529,576 A | 6/1996 | Lundt et al. | |
| 5,534,034 A | 7/1996 | Caspers | |
| 5,565,221 A * | 10/1996 | Caroli | B29C 33/302 |
| | | | 249/165 |
| 5,651,792 A | 7/1997 | Telikicherla | |
| 5,652,053 A | 7/1997 | Liegeois | |
| 5,718,925 A * | 2/1998 | Kristinsson | A61F 2/5046 |
| | | | 264/573 |
| 5,728,165 A | 3/1998 | Brown, Sr. | |
| 5,800,565 A | 9/1998 | Biedermann | |
| 5,824,111 A | 10/1998 | Schall et al. | |
| 5,830,396 A * | 11/1998 | Higgins | A61F 2/30734 |
| | | | 264/109 |
| 5,846,464 A * | 12/1998 | Hoffman | B23Q 1/035 |
| | | | 264/219 |
| 5,880,964 A * | 3/1999 | Schall | A61F 2/5046 |
| | | | 623/27 |
| 5,885,509 A | 3/1999 | Kristinsson | |
| 5,888,215 A | 3/1999 | Roos et al. | |
| 5,888,217 A | 3/1999 | Siemker | |
| 5,944,679 A | 8/1999 | DeToro | |
| 5,980,803 A * | 11/1999 | Slemker | A61F 2/5046 |
| | | | 264/222 |
| 6,033,440 A | 3/2000 | Schall et al. | |
| 6,051,026 A | 4/2000 | Biedermann et al. | |
| 6,206,932 B1 | 3/2001 | Johnson | |
| 6,228,124 B1 | 5/2001 | Slemker et al. | |
| 6,231,618 B1 | 5/2001 | Schall et al. | |
| D453,591 S | 2/2002 | Garden | |
| 6,368,357 B1 | 4/2002 | Schon et al. | |
| 6,412,196 B1 * | 7/2002 | Gross | A43B 13/026 |
| | | | 36/102 |
| 6,443,282 B1 | 9/2002 | Kwoka | |
| 6,444,282 B1 | 9/2002 | Shirer | |
| 6,458,163 B1 | 10/2002 | Slemker et al. | |
| 6,470,552 B1 * | 10/2002 | Slemker | A61F 2/5046 |
| | | | 29/447 |
| 6,497,028 B1 | 12/2002 | Rothschild et al. | |
| 6,500,210 B1 | 12/2002 | Sabolich et al. | |
| 6,576,022 B2 | 6/2003 | Meyer et al. | |
| 6,597,965 B2 * | 7/2003 | Graves | A61F 2/5046 |
| | | | 623/27 |
| 6,669,736 B2 | 12/2003 | Slemker et al. | |
| 6,700,563 B1 | 3/2004 | Koizumi | |
| 6,761,743 B1 | 7/2004 | Johnson | |
| 6,767,332 B1 | 7/2004 | Pardue | |
| 6,942,703 B2 | 9/2005 | Carstens | |
| 6,974,484 B2 | 12/2005 | Caspers | |
| 7,090,700 B2 | 8/2006 | Curtis | |
| 7,105,122 B2 | 9/2006 | Karason | |
| 7,172,714 B2 * | 2/2007 | Jacobson | B29C 33/308 |
| | | | 264/108 |
| 7,239,937 B2 * | 7/2007 | Slemker | A61B 5/107 |
| | | | 600/587 |
| 7,240,414 B2 | 7/2007 | Taylor, Sr. | |
| 7,300,466 B1 | 11/2007 | Martin | |
| 7,318,504 B2 | 1/2008 | Vitale et al. | |
| 7,338,532 B2 | 3/2008 | Haberman et al. | |
| 7,344,567 B2 | 3/2008 | Slemker | |
| 7,402,265 B2 | 7/2008 | Jacobson | |
| 7,479,163 B2 | 1/2009 | Slemker et al. | |
| 7,591,857 B2 | 9/2009 | Slemker et al. | |
| 7,658,720 B2 | 2/2010 | Johnson | |
| 7,677,923 B1 * | 3/2010 | Chen | H01R 12/7029 |
| | | | 439/541.5 |
| 7,753,866 B2 | 7/2010 | Jackovitch | |
| 7,762,973 B2 | 7/2010 | Einarsson et al. | |
| 7,980,921 B2 | 7/2011 | Saravanos | |
| 7,985,192 B2 | 7/2011 | Sheehan et al. | |
| 8,083,807 B2 | 12/2011 | Auberger et al. | |
| 8,088,320 B1 | 1/2012 | Bedard | |
| 8,116,900 B2 | 2/2012 | Slemker et al. | |
| 8,142,517 B2 | 3/2012 | Horie | |
| 8,303,527 B2 | 11/2012 | Joseph | |
| 8,323,353 B1 | 12/2012 | Alley et al. | |
| 8,382,852 B2 | 2/2013 | Laghi | |
| 8,403,993 B2 | 3/2013 | Aram et al. | |
| 8,423,167 B2 * | 4/2013 | Sanders | A61F 2/5046 |
| | | | 623/901 |

(56) References Cited

U.S. PATENT DOCUMENTS

| | | |
|---|---|---|
| 8,465,445 B2 | 6/2013 | George |
| 8,470,050 B2 | 6/2013 | Dillingham |
| 8,535,389 B2 | 9/2013 | McKinney |
| 8,576,250 B2 | 11/2013 | Sabiston et al. |
| 8,894,719 B2 | 11/2014 | Egilsson et al. |
| D723,163 S | 2/2015 | Gottlieb |
| 8,978,224 B2 | 3/2015 | Hurley et al. |
| 9,020,788 B2 * | 4/2015 | Lang ................. A61F 2/30942 703/6 |
| 9,044,349 B2 | 6/2015 | Hurley et al. |
| 9,155,636 B1 | 10/2015 | Fikes |
| 9,265,629 B2 | 2/2016 | Kelley et al. |
| 9,345,590 B2 | 5/2016 | Arabian et al. |
| 9,468,542 B2 | 10/2016 | Hurley et al. |
| 9,468,543 B2 | 10/2016 | Hurley et al. |
| 9,474,633 B2 | 10/2016 | Williams et al. |
| 9,549,828 B2 | 1/2017 | Hurley et al. |
| D778,452 S | 2/2017 | Cespedes et al. |
| 2002/0099450 A1 | 7/2002 | Dean et al. |
| 2002/0183859 A1 * | 12/2002 | Houser ................. A61F 2/7812 623/36 |
| 2003/0178746 A1 * | 9/2003 | Eberle ................... A61F 2/5046 264/257 |
| 2003/0181990 A1 | 9/2003 | Phillips |
| 2003/0216669 A1 * | 11/2003 | Lang .................... A61B 5/4528 600/587 |
| 2004/0076700 A1 * | 4/2004 | Horiguchi ............. A61F 5/5044 425/2 |
| 2004/0133276 A1 * | 7/2004 | Lang .................... A61F 2/30756 623/14.12 |
| 2004/0158332 A1 | 8/2004 | Carstens |
| 2004/0204771 A1 | 10/2004 | Swanson, Sr. |
| 2004/0260402 A1 | 12/2004 | Baldini et al. |
| 2004/0262816 A1 * | 12/2004 | Parks ..................... B29C 43/36 264/500 |
| 2005/0101693 A1 | 5/2005 | Arbogast et al. |
| 2005/0119777 A1 * | 6/2005 | Arbogast .............. A61F 2/5046 700/117 |
| 2005/0149202 A1 | 7/2005 | Schaeffer et al. |
| 2005/0184432 A1 * | 8/2005 | Mead .................... B29C 33/307 264/272.15 |
| 2006/0009860 A1 | 1/2006 | Price, Jr. |
| 2006/0020348 A1 * | 1/2006 | Slemker ................. A61B 5/107 623/33 |
| 2006/0020349 A1 | 1/2006 | Slemker |
| 2007/0004993 A1 | 1/2007 | Coppens et al. |
| 2007/0078523 A1 | 4/2007 | Kholwadwala et al. |
| 2007/0152379 A1 | 7/2007 | Jacobson |
| 2007/0298075 A1 | 12/2007 | Borgia et al. |
| 2008/0161938 A1 | 7/2008 | Gramnas |
| 2008/0262400 A1 * | 10/2008 | Clark ................. A61F 5/05866 602/7 |
| 2008/0269914 A1 * | 10/2008 | Coppens ............... A61F 2/5046 623/33 |
| 2009/0036999 A1 | 2/2009 | Egilsson et al. |
| 2009/0076625 A1 | 3/2009 | Groves et al. |
| 2009/0105844 A1 | 4/2009 | Ortiz |
| 2009/0126742 A1 * | 5/2009 | Summer .................... A61F 5/37 128/848 |
| 2009/0177282 A1 * | 7/2009 | Bureau ................. A61L 27/446 623/16.11 |
| 2009/0240344 A1 | 9/2009 | Colvin et al. |
| 2009/0299490 A1 | 12/2009 | Summit |
| 2010/0016772 A1 | 1/2010 | DeToro et al. |
| 2010/0036300 A1 | 2/2010 | Sheehan et al. |
| 2010/0036505 A1 | 2/2010 | Hassler |
| 2010/0082116 A1 | 4/2010 | Johnson et al. |
| 2010/0160722 A1 | 6/2010 | Kuyava et al. |
| 2010/0244296 A1 * | 9/2010 | Keys ................. B29C 45/14073 264/40.1 |
| 2010/0262054 A1 * | 10/2010 | Summit ................. G06F 17/50 602/14 |
| 2010/0274364 A1 | 10/2010 | Pacanowsky et al. |
| 2010/0280621 A1 * | 11/2010 | Adamo ................. A61F 2/4425 623/17.16 |
| 2011/0022184 A1 | 1/2011 | Slemker et al. |
| 2011/0029096 A1 | 2/2011 | Laghi |
| 2011/0071647 A1 | 3/2011 | Mahon |
| 2011/0071649 A1 | 3/2011 | McKinney |
| 2011/0114635 A1 | 5/2011 | Sheehan |
| 2011/0160871 A1 | 6/2011 | Boone et al. |
| 2011/0232837 A9 | 9/2011 | Ottleben |
| 2011/0320010 A1 | 12/2011 | Vo |
| 2012/0022667 A1 | 1/2012 | Accinni et al. |
| 2012/0041567 A1 | 2/2012 | Cornell |
| 2012/0101417 A1 * | 4/2012 | Joseph ...................... A61F 5/01 602/5 |
| 2012/0101597 A1 | 4/2012 | Bache |
| 2012/0143077 A1 | 6/2012 | Sanders et al. |
| 2012/0165956 A1 | 6/2012 | Li |
| 2012/0191218 A1 | 7/2012 | McCarthy |
| 2012/0215324 A1 | 8/2012 | King |
| 2012/0253475 A1 | 10/2012 | Kelley et al. |
| 2012/0271210 A1 | 10/2012 | Galea et al. |
| 2012/0271214 A1 | 10/2012 | Blanck |
| 2012/0271433 A1 | 10/2012 | Galea et al. |
| 2012/0293411 A1 | 11/2012 | Leithinger et al. |
| 2013/0123940 A1 | 5/2013 | Hurley et al. |
| 2013/0192071 A1 | 8/2013 | Esposito et al. |
| 2013/0197318 A1 | 8/2013 | Herr et al. |
| 2013/0245785 A1 | 9/2013 | Accini et al. |
| 2013/0282141 A1 | 10/2013 | Herr et al. |
| 2013/0295213 A1 * | 11/2013 | Lomicka ............... A61F 2/3094 425/150 |
| 2014/0005798 A1 | 1/2014 | Bache et al. |
| 2014/0005801 A1 | 1/2014 | Van der Watt et al. |
| 2014/0031953 A1 | 1/2014 | MacKenzie |
| 2014/0121783 A1 | 5/2014 | Alley |
| 2014/0149082 A1 | 5/2014 | Sanders et al. |
| 2014/0163697 A1 | 6/2014 | Sanders |
| 2014/0180185 A1 | 6/2014 | Zachariasen |
| 2014/0277584 A1 | 9/2014 | Hurley et al. |
| 2014/0277585 A1 | 9/2014 | Kelley et al. |
| 2014/0379097 A1 | 12/2014 | Hurley et al. |
| 2015/0168943 A1 | 6/2015 | Hurley et al. |
| 2015/0190252 A1 | 7/2015 | Hurley et al. |
| 2015/0265434 A1 | 9/2015 | Hurley et al. |
| 2016/0000587 A1 | 1/2016 | Hurley et al. |
| 2016/0022466 A1 | 1/2016 | Pedtke et al. |
| 2016/0058584 A1 | 3/2016 | Cespedes et al. |
| 2016/0143752 A1 | 5/2016 | Hurley et al. |
| 2016/0235560 A1 | 8/2016 | Cespedes et al. |
| 2016/0334780 A1 | 11/2016 | Dair et al. |
| 2016/0338858 A1 | 11/2016 | Hurley et al. |
| 2017/0027718 A1 | 2/2017 | Williams et al. |
| 2017/0027720 A1 | 2/2017 | Pedtke et al. |
| 2017/0079811 A1 | 3/2017 | Kelley et al. |
| 2017/0079828 A1 | 3/2017 | Pedtke et al. |
| 2017/0095356 A1 | 4/2017 | Hurley et al. |
| 2017/0128238 A1 | 5/2017 | Hurley et al. |
| 2017/0143518 A1 | 5/2017 | Hurley et al. |
| 2017/0143520 A1 * | 5/2017 | Hurley ...................... A61F 2/80 |

FOREIGN PATENT DOCUMENTS

| | | | |
|---|---|---|---|
| EP | 0204407 A2 | 12/1986 | |
| EP | 1433447 | 6/2004 | |
| EP | 1433447 A2 | 6/2004 | |
| GB | 127451 | 6/1919 | |
| GB | 127451 A | 6/1919 | |
| GB | 2080114 | 2/1982 | |
| GB | 2080114 A | 2/1982 | |
| GB | 2080114 A * | 2/1982 | ............... A61F 2/60 |
| SU | 305888 | 6/1971 | |
| WO | 1991/016019 | 10/1991 | |
| WO | 1991016019 | 10/1991 | |
| WO | 1998/012994 | 4/1998 | |
| WO | 1998012994 | 4/1998 | |
| WO | 2000003665 | 1/2000 | |
| WO | 2000003665 A1 | 1/2000 | |
| WO | 2000/030572 | 6/2000 | |
| WO | 2000030572 | 6/2000 | |

(56) References Cited

FOREIGN PATENT DOCUMENTS

| WO | 2001021113 | 3/2001 |
| --- | --- | --- |
| WO | 2007/035875 | 3/2007 |
| WO | 2007035875 | 3/2007 |
| WO | 2008/116025 | 9/2008 |
| WO | 2008116025 | 9/2008 |
| WO | 2009/093020 | 7/2009 |
| WO | 2009093020 | 7/2009 |
| WO | 2012/021823 | 2/2012 |
| WO | 2012021823 | 2/2012 |
| WO | 2014/004709 | 1/2014 |
| WO | 2014004709 | 1/2014 |
| WO | 2014/068269 A1 | 5/2014 |
| WO | 2014068269 | 5/2014 |

OTHER PUBLICATIONS

Koike, K. The TC double socket above-knee prosthesis. Prosthetic and Orthotics International. 1981, 5(3): 129-134.

Comfil (thermoformable composite technique). Fillauer Fabrication Manual. Jun. 15, 2012.

Fairley. From Academia to the Developing World. O&P Edge Magazine. May 2011.

Jana. Designing a cheaper, simpler prosthetic arm. ZDNet. Nov. 14, 2011.

Gleave. A plastic socket and stump casting technique for above-knee prostheses. Hong Kong Medical Department. vol. 47, No. 1, Feb. 1965.

Hwang. Winner-Spark! Spark Galleries. 2012.

Turner. Fit for Everyone. Yank Design. Jul. 17, 2013.

Wilson. Recent Advances in Above-Knee Prosthetics. Artificial Limbs. vol. 12, No. 2, 1968.

Supplementary European Search Report and Opinion dated Jul. 21, 2015, for application EP 12847452.5 filed Nov. 13, 2012.

Alley, "The High-Fidelity Interface: Skeletal Stabilization through Alternating Soft Tissue Compression and Release", Myoelectric Symposium 2011, New Brunswick, Canada, Aug. 14-19, 2011. (3 pages).

Andrysek, "Lower-limb prosthetic technologies in the developing world: a review of literature from 1994-2010", Prosthetics and Orthotics International, Cardiff, Wales, UK; Dec. 2010; 34(4): pp. 378-398. (21 pages).

Burgess, et al., "The Management of Lower-Extremity Amputations: Surgery: Immediate Postsurgical Prosthetic Fitting: Patient Care", Superintendent of Documents, U.S. Government Printing Office, Washington DC 20402 Publication prepared for the Prosthetic and Sensory Aids Service, Dept. of Medicine and Surgery, Veterans Administration, Washington, D.C., Aug. 1969. (129 pages).

Conn, "Materials Science: A Look At Some of the Substances on the Market for Device Fabrication", O&P Almanac, Jun. 2012, pp. 28-31; downloaded from http://www.allardusa.com/pdf/articles/Materials%20Science%20Article%20-%20June%202012%20O%26P%20Almanac.pdf. (4 pages).

Fairley, "M.A.S. Socket: A Transfemoral Revolution", The O&P Edge, Jun. 2004; downloaded from www.oandp.com/articles/2004-06-03.asp. (4 pages).

Gard, "Overview of Lower Limb Prosthetics Research", WRAMC and the VA Orthopedic & Prosthetic Workshop, Arlington, VA, Nov. 17 and 18, 2003, pp. 1-48. (49 pages).

Geil, M.D. "Consistency, precision, and accuracy of optical and electromagnetic shape-capturing systems for digital measurement of residual-limb anthropometrics of persons with transtibial amputation", Journal of Rehabilitation Research and Development, vol. 44, No. 4 (2007); pp. 515-524, U.S.A. (10 pages).

Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. (1 page).

Greenwald, et al., "Volume Management: Smart Variable Geometry Socket (SVGS) Technology for Lower-Limb Prostheses", JPO Journal of Prosthetics and Orthotics, vol. 15, No. 3 (2003), pp. 107-112, U.S.A. (6 pages).

Hanger Comfortflex Socket System for Prosthetic Devices: website pages downloaded Nov. 28, 2012 from http://www.hanger.com/prosthetics/services/Technology/Pages/ComfortFlex.aspx. (2 pages).

Hong, et al., "Dynamic Moisture Vapor Transfer through Textiles: Part I: Clothing Hygrometry and the Influence of Fiber Type", Textile Research Journal, Thousand Oaks, California, U.S.A., Dec. 1988; 58: 697-706, Abstract. (1 page).

Initial and Interim Prostheses, Otto Bock Healthcare LLP, Prosthetics Lower Extremities 2008, (Feb. 2013) pp. 1-8, www.ottobockus.com/cps/rde/xbcr/ob_us_en/08cat_1.pdf.

Krouskop, et al., "Computer-aided design of a prosthetic socket for an above-knee amputee", Journal of Rehabilitation Research and Development, vol. 24, No. 2 (Spring 1987) pp. 31-38, U.S.A. (8 pages).

Manucharian, "An Investigation of Comfort Level Trend Differences Between the Hands-On Patellar Tendon Bearing and Hands-Off Hydrocast Transtibial Prosthetic Sockets", JPO: Journal of Prosthetics and Orthotics, Washington, D.C., U.S.A.; vol. 23, No. 3, 2011: pp. 124-140. (17 pages).

Ottobock: PU Resin Kit Polytol; downloaded Dec. 17, 2012 from http://www.ottobock.com/cps.rde/xchg/ob_com_en/hs.xsl/17414.html. (2 pages).

PCT Search Report and Written Opinion dated Jun. 13, 2014, for International Application No. PCT/US2014/029773, 14 pages.

Sanders, et al., "Residual limb vol. change: Systematic review of measurement and management", Journal of Rehabilitation Research & Development, 2011, vol. 48: pp. 949-986, U.S.A. (29 pages).

Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 7, Issue 1; pp. 71-74, abstract. (1 page).

SBIR topic summary: "Pro-Active Dynamic Accomodating Socket", SITIS archives topic No. OSD08-H18 (OSD); http://www.dodsbir.net/sitis/archieves_display_topic.asp?Bookmark=34570; downloaded and printed Mar. 25, 2013, U.S. A. (4 pages).

Smith, M. , "Silver Linings for O&P Devices", The Academy Today, vol. 1, No. 4: Oct. 2005; downloaded from http://www.oandp.org/AcademyTODAY/2005Oct/7.asp. (4 pages).

Spaeth, JP, "Laser imaging and computer-aided design and computer-aided manufacture in prosthetics and orthotics", Physical Medicine and Rehabilitation Clinics of North America, Elsevier Publishing, Amsterdam, The Netherlands; Feb. 2006 17(1): 245-263, abstract. (2 pages).

Wilson Jr., "A Material for Direct Forming of Prosthetic Sockets", downloaded from http://www.oandplibrary.org/al/1970_01_053.asp; downloaded Dec. 14, 2012. (4 pages).

Wu, et al., "CIR sand casting system for trans-tibial socket", Prosthet Orthol Int. Aug. 2003: 27(2): 146-52, abstract. (1 page).

International Search Report in connection with International Patent application No. PCT/US2012/064876, dated Feb. 19, 2013, 1-6.

Written Opinion in connection with International Patent application No. PCT/US2012/064876, dated Feb. 19, 2013, 1-10.

Compton, Compton table. "New plastics for forming directly on the patient." Prosthetics and Orthotics International, 1978, vol. 2, No. 1, pp. 43-47.

Fairley, Miki. Socket can be fabricated, modified, fitted-in one hour. O&P Edge Magazine. Jun. 2007.

Allard. Cut-4-Custom: Custom TLSO in less than an hour. O&P Edge Magazine. Jul. 2010.

Instamorph. Remoldable prosthetics. Apr. 2013. <www.instamorph.com/ideas/outdoors-and-ergonomics/remoldable-prosthetics>.

Kelley et al. U.S. Appl. No. 61/794,948, filed Mar. 15, 2013.

Alley, "The high-fidelity interface: Skeletal stabilization through alternating soft tissue compression and release," Myoelectric Symposium, Aug. 14-19, 2011 (3 pages).

Andrysek, "Lower-limb prosthetic technologies in the developing world: a review of literature from 1994-2010," Prosthetics and orthotics international, 34(4):378-398, Dec. 1, 2010.

(56) References Cited

OTHER PUBLICATIONS

Burgess et al., "The Management of Lower-Extremity Amputation: Surgery: Immediate Postsurgical Prosthetic Fitting: Patient Care," Superintendent of Documents, U.S. Government Printing Office, Washington D.C., publication prepared for the Prosthetic and Sensory Aids Service Dept of Medicine and Surgery, Veterans Administration, Aug. 1969 (129 pages).
Comfil (thermoformable composite technique). Fillauer Fabrication Manuel. Jun. 15, 2012.
Compton et al., "New plastics for forming directly on the patient," Prosthetics and orthotics international, 2(1):43-47, Apr. 1978.
Conn, "Materials Science: A look at Some of the Substances on the Market for Device Fabrication," O&P Almanac, pp. 28-31, Jun. 2012.
Fairley, "From Academia to the Developing World," downloaded from <http://www.oandp.com/articles/2011-05_03.asp>, The O&P Edge, 5 pages, May 2011.
Fairley, "M.A.S. Socket: A Transfemoral Revolution," downloaded from <http://www.oandp.com/articles/2004-06_03.asp>, The O&P Edge, 3 pages, Jun. 2004.
Fairley, "Socket can be fabricated, modified, fitted—in one hour," downloaded from <http://www.oandp.com/articles/2007-06_09.asp>, The O&P Edge, 3 pages, Jun. 2007.
Fillauer LLC and Centri® "Comfil® Thermo Formable Composite Technique" Fillauer Fabrication Manuel, 14 pages, Jun. 15, 2012.
Gard, "Overview of Lower Limb Prosthetics Research," WRAMC and the VA Orthopedic & Prosthetic Workshop, Arlington, VA, 49 slides, Nov. 17, 2003.
Allard USA, "Cut-4-Custom: Custom TLSO in Less Than an Hour," O&P Edge Magazine, downloaded from the Internet: <URL: http://www.oandp.com/articles/news_2010-07-01_24.asp>, 2 pages, Jul. 2010.
Koike et al., "The TC double socket above-knee prosthesis," Prosthet Orthot Int., 5(3):129-134, Dec. 1981.
Krouskop et al., "Computer-aided design of a prosthetic socket for an above-knee amputee," J Rehabil Res Dev., 24(2):31-38, 1987.
Manucharian, "An investigation of comfort level trend differences between the hands-on patellar tendon bearing and hands-off hydrocast transtibial prosthetic sockets," J Prosthet Orthot., 23(3):124-140, Jul. 1, 2011.
Ottobock, "Initial and interim prostheses" Prosthetics Lower Extremities 2008, downloaded from the internet: <URL: http://www.ottobockus.com/cps/rde/xbcr/ob_us_en/08cat_4.pdf> on Feb. 2013, pp. 24-26.
Ottobock, "PU Resin Kit Polytol®" downloaded from the internet: <URL: http://www.ottobock.com/cps/rde/xchg/pb_com_en/hs.xsl/17414.html> on Dec. 17, 2012, 2 pages.
Quigley, "Prosthetics Management: Overview, Methods and Materials," Chapter 4, Atlas of Limb Prosthetics: Surgical, Prosthetic, and Rehabilitation Principles, (Second Edition), 19 pages, 1992.
Sanders et al., "Residual limb volume change: Systematic review of measurement and management," J Rehabil Res Dev., 48(8):949-986, 2011.
Sathishkumar et al., "A cost-effective, adjustable, femoral socket, temporary prosthesis for immediate rehabilitation of above-knee amputation," Int J Rehabil Res., 27(1):71-74, Mar. 1, 2004 [abstract only].
Sbir, "Pro-Active Dynamic Accommodating Socket" Solicitation Topic Code: OSD08-H18, 2 pages, Solicitation Year: 2008.
Smith, "Silver Linings for O&P Devices" The Academy TODAY, 1(4):A-8-A-9, Oct. 2005.
Spaeth, "Laser imaging and computer-aided design and computer-aided manufacture in prosthetics and orthotics," Phys Med Rehabil Clin N Am., 17(1):245-263, Feb. 28, 2006 [abstract only].
Geil, "Consistency, precision, and accuracy of optical and electro-magnetic shape-capturing systems for digital measurement of residual-limb anthropometrics of persons with transtibial amputation," J Rehabil Res Dev., 44(4):515-524, May 20, 2007.
Gerschutz et al., "Mechanical Evaluation of Direct Manufactured Prosthetic Sockets," American Academy of Orthotists & Prosthetists, 38th Academy Annual Meeting and Scientific Symposium, USA, <URL: http://oandp.org/publications/iop/2012/2012-19.pdf>, 1 pages, Mar. 21, 2012.
Gleave, "A plastic socket and stump casting technique for above-knee prostheses," J Bone Joint Surg Br., 47:100-103, Feb. 1965.
Greenwald et al., "Volume Management: Smart Variable Geometry Socket (SVGS) Technology for Lower-Limb Prostheses," JPO: Journal of Prosthetics and Orthotics, 15(3):107-112, Jul. 1, 2003.
Hanger Inc., "ComfortFlex Socket System," downloaded from http://www.hanger.com/prosthetics/services/Technology/Pages/ComfortFlex.aspx, archived Sep. 17, 2012.
Hanger Prosthetics & Orthotics [online] "ComfortFlex Socket System," downloaded from the internet: <URL: http://www.hanger.com/prosthetics/services/Technology/Pages/ComfortFlex.aspx> on Nov. 28, 2012, 2 pages.
Hong et al., "Dynamic moisture vapor transfer through textiles part I: clothing hygrometry and the influence of fiber type," Textile Research Journal, 58(12):697-706, Dec. 1, 1988 [abstract only].
Hwang [designer], "Blooming Winner-Spark!" Spark Galleries, 3 pages, 2012.
Instamorph, "Moldable Plastic: Instructions"downloaded from URL: <http://www.instamorph.com/instructions>, 2 pages, archived Dec. 24, 2011.
Jana, "Designing a cheaer, simpler prosthetic arm," ZDNet [online], <URL: http://www.zdnet.com/article/designing-a-cheaper-simpler-prosthetic-arm/> 3 pages, Nov. 14, 2011.
Turner, "Fit for Everyone," Yanko Design [online], <URL:http://www.yankodesign.com/2013/07/17/fit-for-everyone/>, 7 pages, Jul. 17, 2013.
Wilson et al., "Recent advances in above-knee prosthetics," Artif. Limbs., 12(2):1-27, Jan. 1, 1968.
Wilson Jr., "A material for direct forming of prosthetic sockets," Artif. Limbs., 14(1):53-56, Jan. 1, 1970.
Wu et al., "Technical note: CIR sand casting system for trans-tibial socket," Prosthet Orthot Int., 27(2):146-152, Aug. 2003.
Zhang, "Ethylene-vinyl acetate copolymer based on a continuous phase of dual/polycaprolactone blend of the porous material prepared," Yangzhou University, Materials Science, Master's Thesis, [USPTO translation of relevant portions of Zhang article], 131 pages, 2010.

* cited by examiner

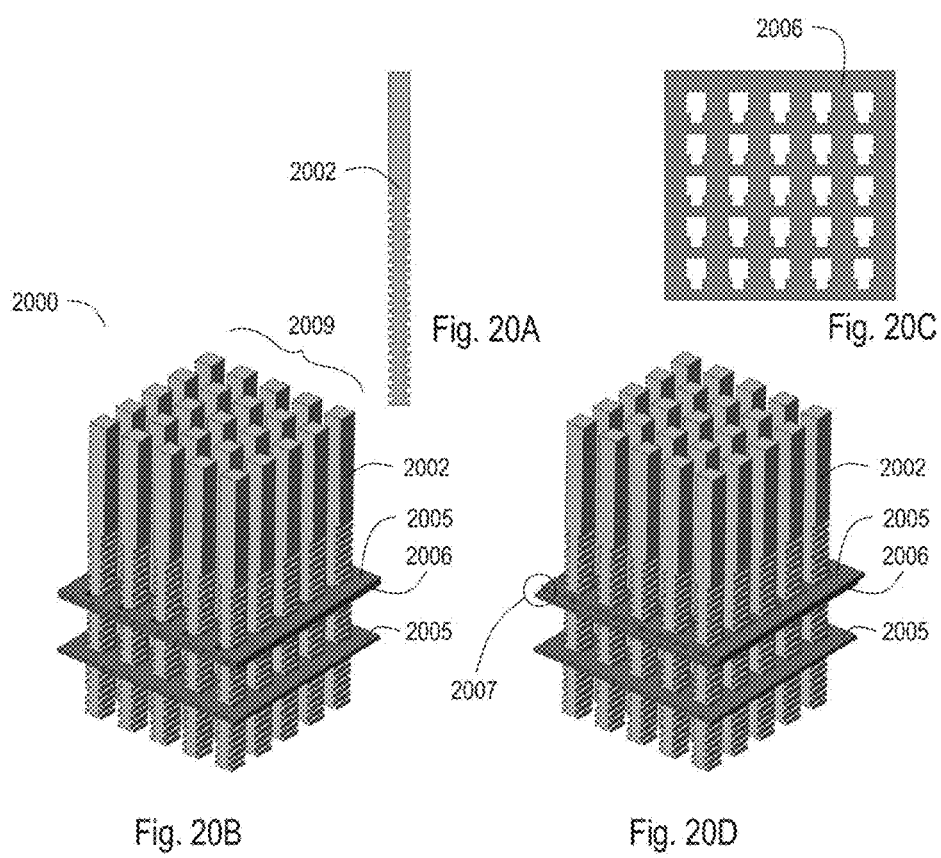

METHOD AND APPARATUS FOR TRANSFERRING A DIGITAL PROFILE OF A RESIDUAL LIMB TO A PROSTHETIC SOCKET STRUT

CROSS-REFERENCE TO RELATED APPLICATIONS

This application claims priority to U.S. Provisional Patent Application Nos. 62/007,742, entitled "Apparatus and method for transferring a digital profile of a residual limb to a prosthetic socket strut," filed on Jun. 4, 2014; 62/045,433, entitled "Improvements for a modular prosthetic socket: soft good arrangements, hardware, and a flexible inner liner," filed on Sep. 3, 2014; and 62/128,218, entitled "Improvements for a modular prosthetic socket: soft good arrangements, hardware, and a flexible inner liner," filed on Mar. 4, 2015. All the above-referenced patent applications are hereby fully incorporated by reference herein. Additionally, all other publications, patents and patent applications identified in this specification are herein incorporated by reference to the same extent as if each such individual publication or patent application were specifically and individually indicated to be so incorporated by reference.

TECHNICAL FIELD

The technology relates to an apparatus and method for transferring a digital profile of a body part to a thermally reformable thermoplastic article.

BACKGROUND

Prosthetic limbs for the upper and lower extremities typically include a residual limb socket, an alignment system, and distal prosthetic components to complete the limb. For any prosthetic limb, the prosthetic socket is the portion of the prosthesis that is designed to fit on the residual limb and connect with the rest of the prosthetic components. The prosthetic socket grasps the residual limb and provides the functional connection to the distal components. If the prosthetic socket does not fit properly, it will inevitably be uncomfortable for the patient, even to a level of intolerability. Even the most sophisticated of prosthetic limb components will not serve the patient well, if the fit of the socket is unsatisfactory.

Conventional prosthetic sockets are typically custom made, making use of positive molds derived from a cast of the patient's limb. The positive mold, standing in for the patient's limb, is used to make the prosthetic socket and is often saved for future use by the prosthetic shop. Although the custom fitting and positive mold making process can work well, if performed by a highly skilled practitioner, the process and resulting positive mold can be quite costly, due in part to the time, space, and expense needed to make, store and ship the cumbersome positive mold.

Some of the shortcomings of the conventional approach to fabricating custom-fitted prosthetics are addressed by the development of a modular approach to socket assembly, as disclosed in U.S. Patent Application Publication No. 2013/0123940 of Hurley and Williams, filed on Nov. 13, 2012, and U.S. patent application Ser. No. 14/213,788 of Hurley and Williams, filed on Mar. 14, 2014. Modular components that vary in size and shape can be fabricated by modern, scalable manufacturing methods. Assembling these components into custom-fitted prosthetic sockets can occur within a single day, in contrast to the multiple weeks needed for conventional prosthetic socket fabrication methods. Nevertheless, challenges remain in the full implementation of a modular approach to prosthetic socket assembly. For example, manufacturing and assembly facilities, prosthetic socket clinical sites, and patients can often be widely scattered from each other geographically and logistically.

Therefore, it would be very desirable to have improved methods and apparatus for designing and manufacturing prosthetic sockets. Ideally, such improved methods and apparatus would be able to fully replace the use of positive molds with efficient and effective methods for fitting prosthetic sockets to patients' residual limbs. It would also be ideal if these methods and apparatus could reduce the transactional costs associated with the flow of information and components between patients, doctors, prosthetists and manufacturers. At least some of these objectives will be met by the embodiments described below.

SUMMARY

According to one aspect of the technology, a thermal reforming apparatus includes a reconfigurable pin tool device and a molding rig coupled to the pin tool device that secures a thermoplastic article to be altered, reshaped, or contoured by the reconfigurable pin tool device. Embodiments of the reconfigurable pin tool device may include a pin plate having multiple pin holes, multiple pins vertically and slidably aligned through the pin holes of the pin plate, such that the pins are arranged as a pin field, an upper surface of the pin field comprising a molding surface. A reconfigurable pin tool device embodiment may further include a pin movement resistance mechanism disposed proximate the pin plate, the movement resistance mechanism being adjustable to vary a level of resistance to applied force on the pins such that the molding surface provides sufficient resistance to serve as a mold for a thermally malleable thermoplastic article pressed against it. Embodiments of a molding rig may include a thermoplastic article holding assembly and a compliant molding press arranged to press the thermoplastic article against the molding surface.

In some embodiments of the thermal reforming apparatus, the pin movement resistance mechanism includes a pressurized container holding a pool of an elastomeric composition into which a portion of each of the multiple pins is immersed. One example of a suitable elastomeric composition is silicon.

In particular embodiments, the pressurized container of the pin movement resistance mechanism is adjustable between an unpressurized state and a pressurized state. The multiple pins of the reconfigurable pin tool are freer to slide through the multiple pin holes when the pressurized container is in the unpressurized state than when it is in the pressurized state. In typical embodiments, when the pressurized container is in the unpressurized state, the pins are vertically stable against gravity.

In some embodiments of the apparatus, the molding surface is configurable into a desired profile for a reformed thermoplastic article, such desired profile typically being a replicate or a complement of a profile of at least a portion of a body part.

In some embodiments, the thermal reforming apparatus (or a larger system that includes the apparatus) includes a CNC machine having a robotic arm that is operable to press down on each of the pins in the pin field to a desired elevation.

According to a second aspect of the technology, a method of reforming a thermoplastic article to assume a desired shape provides a series of steps, such steps including heating a thermoplastic article to render it malleable, and placing the thermoplastic article against a molding surface having a desired shape that replicates a portion of a body part. Embodiments of the method may continue by pressing the malleable thermoplastic article against the molding surface with a compliant molding press to reform at least a portion of the thermoplastic article into the desired shape, and subsequently removing the reformed thermoplastic article from the molding surface, the reformed thermoplastic article retaining the desired shape after removal from the molding surface.

In some embodiments of the method of reforming a thermoplastic article, the thermoplastic article includes at least a portion of medical device; in some embodiments, the thermoplastic article includes a component of a prosthetic device; in particular embodiments, the thermoplastic article is a strut for a prosthetic socket.

In some embodiments of the method of reforming a thermoplastic article, the body part comprises a residual limb or a portion thereof.

In some embodiments of the method of reforming a thermoplastic article, the thermoplastic article comprises a thermoplastic-fiber composite. In particular examples of thermoplastic fiber composite composition, the fiber of the thermoplastic-fiber composite includes multiple continuous fibers. In further particular embodiments, all or substantially all of the fiber in the composition is in a continuous form.

In some embodiments of the method of reforming a thermoplastic article, prior to removing the article from the molding surface, the method includes allowing the thermoplastic article to cool sufficiently such that the thermoplastic article retains the desired shape once it is removed from the molding surface.

In some embodiments of the method of reforming a thermoplastic article, prior to the heating the article and placing it against the molding surface, the method may include acquiring digital data representing the portion of the body part; and using the digital data to form the molding surface into the desired shape that replicates the body part.

In some embodiments of the method, the molding surface includes or substantially consists of end points or facets of positionable pins, and using the digital data to form the molding surface includes using a CNC machine to adjust positions of the pins. In other embodiments, using the digital data includes moving the pins individually using a motor.

According to a third aspect of the technology, a method of transferring a digital profile of a residual limb to a prosthetic socket strut may include acquiring digital data that profiles a residual limb and packaging that digital residual limb data for downstream use. Downstream, embodiments of the method may include orienting the digital limb data for downstream use onto a prosthetic socket structure, and then applying the digital data to a thermal reforming a modular prosthetic socket strut to render a reformed strut, the reformed strut replicating or being complementary to a portion of the residual limb.

According to a fourth aspect of the technology, a method of fabricating a prosthetic socket that makes use of a thermally reformed socket strut may include acquiring residual limb digital data that represents a profile of at least part of the residual limb; and then processing the residual limb digital data to provide prosthetic socket structure data representing at least part of the prosthetic socket. Embodiments of the method may continue by using the prosthetic socket structure digital data to thermally reform the prosthetic socket strut from a first, initial configuration to a second, reformed configuration, wherein the strut in the second, reformed configuration conforms to a portion of the residual limb.

In some embodiments of the method of fabrication a prosthetic socket, the residual limb digital data comprises a profile of an external, three dimensional, physical boundary of the residual limb. In particular embodiments, the residual limb digital data may further include a profile of compliance of tissue underlying the external, physical boundary of the residual limb.

In a further step, embodiments of the method may include assembling a complete prosthetic socket, making use of the strut in the reformed configuration.

BRIEF DESCRIPTION OF THE FIGURES

FIG. 5A shows plates loosened or spaced apart, a condition in which pins can move freely.

FIG. 5B shows plates tightened, thereby pressuring the silicon bed, a condition that stabilizes the pins in place.

FIG. 5C shows a detail view of the reconfigurable pin tool device that clarifies distinctions between the individual pins, the pin field as a whole, and an actuatable molding surface that is formed by the upper surfaces of pins throughout the entire pin field.

FIG. 8 shows the reconfigurable pin tool prior to CNC actuation of the pins; the pins are thus in a neutral position, the pin bed is flat.

FIG. 9 shows the reconfigurable pin tool after CNC actuation of the pins; the pin bed formed by the pins now has a desired contour.

FIG. 10 shows an embodiment of an assembled apparatus for thermally reforming a thermoplastic article; a molding rig is now placed on top of the reconfigurable pin tool. A heated thermoplastic article is in place within the molding rig; this view is prior to downward application of pressure to the strut by the pressure bladder.

FIG. 11 shows the assembled apparatus as in FIG. 10 after expansion of a pressure bladder, which is now expanded downward against the raised pins.

FIG. 18A shows a low angle top perspective view of the apparatus.

FIG. 18B shows a side view of the circumferentially operable reconfigurable pin tool apparatus.

FIG. 18C shows a steep angle top perspective view of the circumferentially operable reconfigurable pin tool apparatus.

FIG. 19A shows an isometric view of an embodiment of a circumferentially operable reconfigurable pin tool apparatus.

FIG. 19B shows a steep top down perspective view of an embodiment of a circumferentially operable reconfigurable pin tool apparatus.

FIG. 19C shows a side view of an embodiment of a circumferentially operable reconfigurable pin tool apparatus.

FIG. 19D shows a top perspective view of an embodiment of a circumferentially operable reconfigurable pin tool apparatus that focuses on an upper portion thereof, focusing on centrally positioned inflatable rubber cone and a metal plate disposed along the internal ends of an array of inwardly directed pins.

FIG. 19E shows a side view of detail of an embodiment of a circumferentially operable reconfigurable pin tool apparatus, focusing on the internal ends of inwardly directed pins that have been fitted with gimbaled plates, the plates engaging a sheet of malleable sheet metal and foam layer that intervene against a target article to be reformed.

FIG. 19F shows a side view of an embodiment of an target article positioned over a central inflatable positive molding dummy, in the context of the arrangement shown in FIG. 19D.

FIG. 20A shows a side profile view of a square pin with slots on two opposing sides.

FIG. 20B shows an array of pins arranged as a pin bed within a series of plates, top and bottom aligning plates and an off-settable plate FIG. 20C shows an aligning plate with square or rectangular holes that allow free through-movement of slotted pins when the pins are appropriately centered, but which brakes pin movement when moved laterally with respect to upper and lower alignment plates.

FIG. 20D is similar to FIG. 20B, but depicts the relative position of the offset plate after it has been moved laterally to brake pin movement.

FIG. 29 shows a use two sets of pin, set to male and female, and compress material in between.

DETAILED DESCRIPTION OF THE INVENTION

Figure 1:
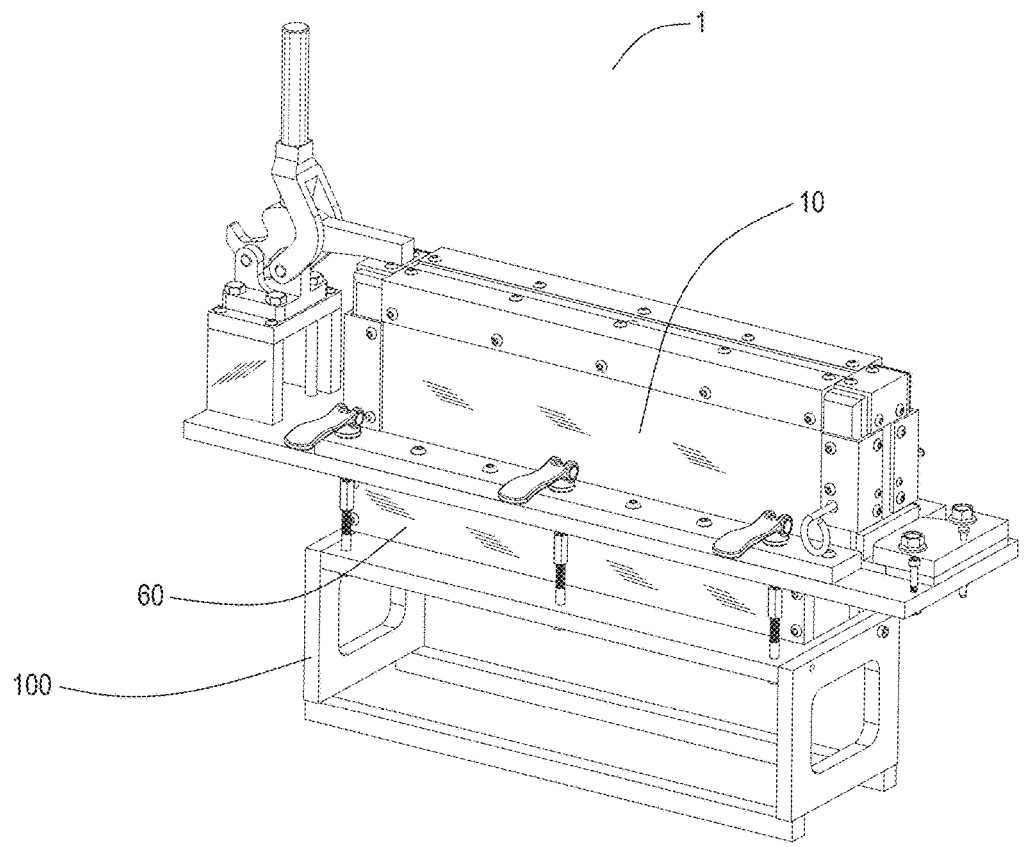
FIG. 1 shows a perspective view of an embodiment of an apparatus for thermally reforming a thermoplastic article to conform to a desired profile.

An apparatus that transfers the contours of a body portion to an article that replicates the contours into a complementary contour on or within an article is described herein. Embodiments include an actuated surface, more particularly an actuated surface formed by an array of facets, as may be embodied as the end surfaces of an array of pins. Method embodiments may apply such an actuated surface toward a target surface of a thermoplastic article. Such thermoplastic articles also include fiber, such that the at least one actuated surface of an apparatus engages a thermoplastic fiber composite article, and reforms it to assume a contour that complements the contour of a portion of the body.

Exemplary embodiments of an actuated surface technology provided herein are thermal reforming apparatuses and methods for replicating a known contour onto a thermoplastic article. Embodiments of the apparatus may be referred to as a reconfigurable surface, a reconfigurable pin tooling device, a pin jig, or any similar term or combination of terms. In particular embodiments, a thermal reforming apparatus replicates a contour of a body part, such as a residual limb, onto a thermoplastic or thermoplastic-fiber composite article, such as a strut for a modular prosthetic socket. Embodiments of such a modular prosthetic socket are described in U.S. Pat. No. 8,978,224 of Hurley and Williams; further details of prosthetic socket structure and a thermoplastic fiber composite strut included therein are described in U.S. patent application Ser. No. 14/213,788 of Hurley and Williams.

More generally, the technology described herein relates to a system that acquires a digital profile of a body part, such as a residual limb, and packages or processes that digital profile into data that are appropriate for downstream use. These data, suitable for downstream method use, are developed by using the digital profile of the body part in conjunction with algorithms that apply functions based on biomechanical and medical considerations, as well as product-specific input. Some aspects of a related system and method for assembling a modular prosthetic socket based on metrics of a patient's residual limb are described in U.S. patent application Ser. No. 14/572,571 of Hurley and Pedtke, filed on Dec. 16, 2014.

The disclosed technology also relates to a device, system, and method for digitally profiling a residual limb. In downstream aspects of the technology, the processed digital profile of a residual limb ultimately provides input to the operation of machinery that translates the digital profile of the residual limb into a tangible product or product component. This latter stage of the technology, where digital data controls the operation of manufacturing machinery, is exemplified by the thermal reforming apparatus and associated methods noted above.

FIGS. 1-7 and FIGS. 8-11 show aspects and embodiments of an exemplary reconfigurable pin tool, more particularly a thermal contour reforming apparatus and methods of operating the apparatus. Thermal contour reforming apparatus may also be more generally referred to as a contour replicating apparatus. Examples of the apparatus described herein are particularly directed toward thermally reforming a thermoplastic article, but may also be more generally understood as a contour replicating apparatus. FIGS. 8-11 show the apparatus at various stages during its thermal reforming operation, where it is reshaping a subject thermoplastic article. In particular embodiments and as exemplified herein, the thermoplastic article is a thermoplastic-fiber composite strut (FIGS. 7A-7B), appropriate for incorporation into a modular prosthetic socket.

In various applications of the thermal reforming apparatus, a subject or target thermoplastic article may be any component of a prosthetic socket other than a strut, such as, merely by way of example, a brim element, a distal support cup, or a socket liner. A subject thermoplastic article may also include an orthotic device or brace, or a component of a larger medical device or article that a patient engages with his or her body, such as an exoskeletal device, a wheelchair, ordinary chair, walker, or the like.

Beyond the realm of prosthetic and orthotic devices, a thermoplastic article may be any type of medical device, such as an orthopedic device. With regard to orthopedic devices: most examples of embodiments of the invention provided herein pertain to prosthetic devices and their components, however the scope of the invention includes any medical device that has a portion for which it is advantageous to be sized and contoured to replicate or be complementary to a portion of body part, and which can be rendered in a thermoplastic form. By way of example, arthroscopic procedures include the repair of joint cartilage damaged by arthritis. Some of these procedures include implanting a synthetic plug into the site of damaged cartilage. It would be advantageous for such a synthetic plug to be precisely tailored to the site of damage. Accordingly, a site of arthritic damage can be scanned arthroscopically to create a digital profile of the site. A custom-tailored plug is then prepared for implant by methods described herein from such a digital profile. During a procedure in which the damaged cartilage is being removed, a custom fabricated plug can be implanted immediately.

Beyond the realm of medical devices, a thermoplastic article may be any wearable article. Most generally, a subject thermoplastic article may be one in which reforming of a basic shape into a more particular or desired shape is advantageous. Typically, the exemplary application of the technology described herein is one in which the desired shape is one that replicates the external form of an anatomical region or body portion, but the desired shape need not necessarily be related to an anatomical feature. And still further, the desired shape need not be replicative of any already existing form, but rather a shape purely derived from any design, functional, or aesthetic considerations.

Embodiments of a reconfigurable pin tool and alternative embodiments as described herein belong to a class of "rapid manufacturing machines". The term refers to machines that are rapid in comparison to conventional machines and that generally make use of a digital input. The rapidity of manufacturing machines in producing wearable articles is in comparison to producing individually customized wearable articles or medical devices, which, by conventional approaches, would be made in a one-by-one artisan-like manner, typically involving a highly intensive use of time, money, material resource, and space. The efficiency of such machines can be addressed strictly in terms of creating complex contours, which typically require specific tools that are highly constrained with regard to deviating from a single contour. Rapid manufacturing machines are particularly suitable for producing articles with contours that are specifically desired and need to be produced just once.

Examples of rapid manufacturing machines other than the actuated surface technology or reconfigurable pin tools, as provided here, include 3D printing devices, laser sintering machines, and the like. As used herein, rapid manufacturing machines are typically but not exclusively dedicated to replicating a contour of a portion of a body onto an article or a portion or component thereof. Typically, the replicated contour is actually a complement of the original contour on the body; for example, a convex body contour is replicated as a complementary concave contour.

Further aspects of rapid manufacturing machines as well as further examples of wearable articles manufacturable by such machines are provided in U.S. Provisional Patent App. No. 62/160,158 of Dair et al., as filed on May 12, 2015, which is hereby incorporated into this application by this reference, in its entirety.

Figure 4:
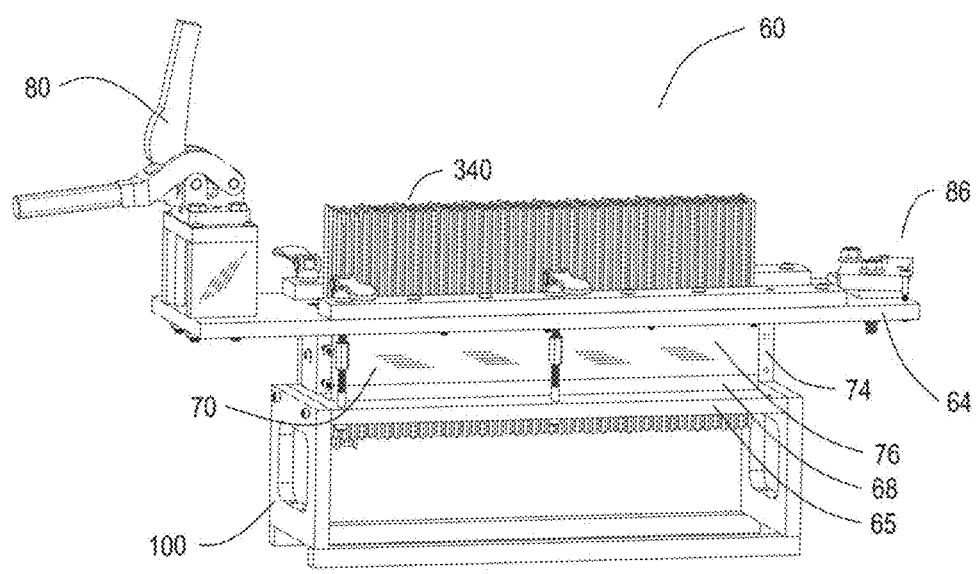
FIG. 4 shows a side perspective view of an embodiment of a reconfigurable pin tool machine similar to that of FIG. 3B, but showing further detail.

Referring first to FIGS. 1-4 in an overview manner: FIG. 1 shows a perspective view of one embodiment of an apparatus 1 for thermally reforming a thermoplastic article to conform to a desired profile. FIGS. 2A-2B show side views of the major subassemblies of apparatus 1 for thermally reforming a thermoplastic article; FIG. 2A shows one embodiment of an isolated molding rig 10, and FIG. 2B shows one embodiment of a reconfigurable pin tool 60. FIGS. 3A-3B show the same components as in FIGS. 2A-2B, but in a perspective view. FIG. 4 shows a side perspective view of an embodiment of a reconfigurable pin tool device 60 with side plates 16 and further detail.

Referring now to FIG. 1 in more detail, thermal contour reforming apparatus 1 may include three basic components: a molding rig 10 and a reconfigurable pin tool 60 that is supported by a base 100. Thermal contour reforming apparatus 1 may be placed under the operable control of a computer numerical control (CNC) machine 200 (see FIG. 6). Molding rig 10 is a removable and connectable component of subassembly of apparatus 1. When apparatus 1 is fully assembled, molding rig 10 is positioned above reconfigurable pin tool 60, and clamped thereto. Now referring to FIG. 2A, molding rig 10 includes a cap plate 12, end plates 14, and side plates 16. Disposed within molding rig 10 and proximate cap plate 12 is a compliant molding press 30. In this particular embodiment, compliant molding press 30 is an inflatable pressure bladder. Also disposed within molding rig 10 is a strut holding assembly 40 that includes a hinge wedge 42, a strut receiver clamp plate 43, a pivot block 46, and a pivot pin 47.

Figure 2A:
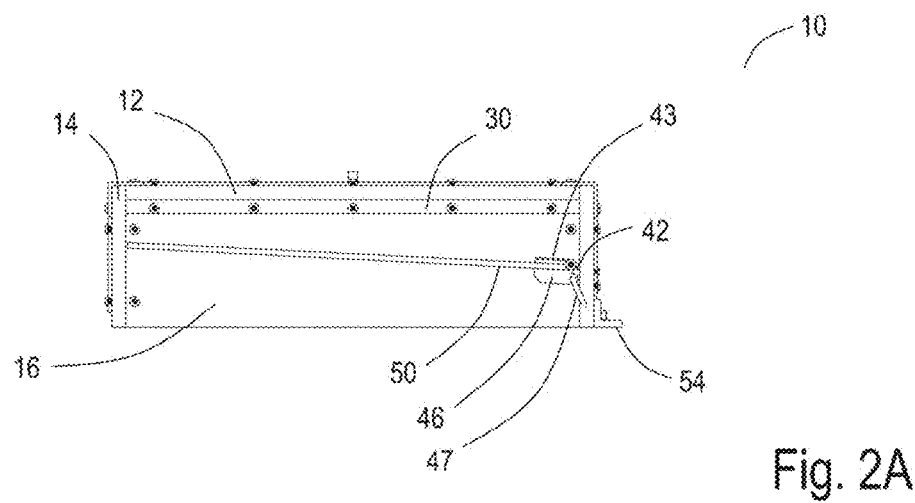
FIG. 2A shows a side view of a molding rig embodiment, a subassembly of an embodiment of an apparatus for thermally reforming a thermoplastic article.
Figure 2B:
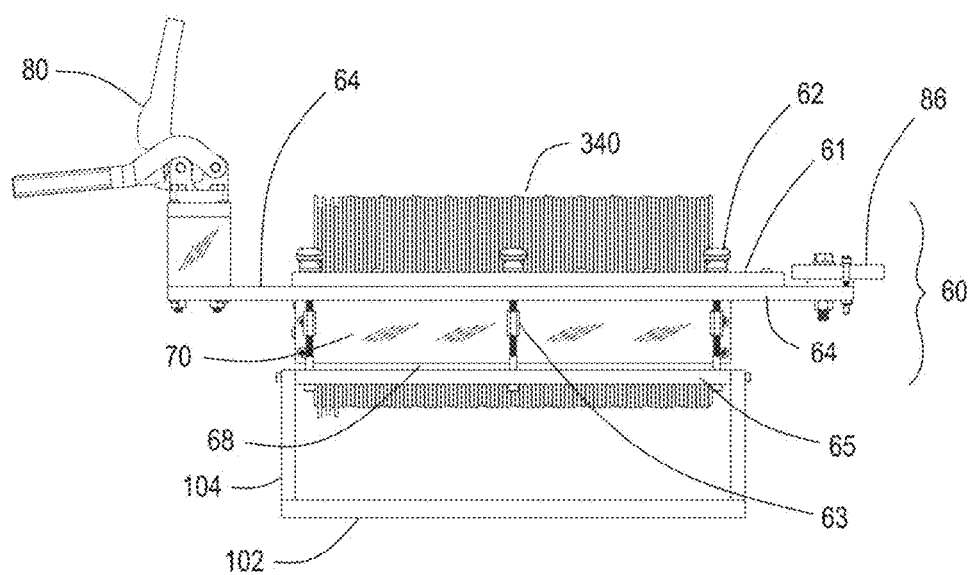
FIG. 2B shows side view of an embodiment of a reconfigurable pin tool or pin jig, a subassembly of apparatus for thermally reforming a thermoplastic article, used in conjunction with the molding rig embodiment of FIG. 2A.
Figure 3A:
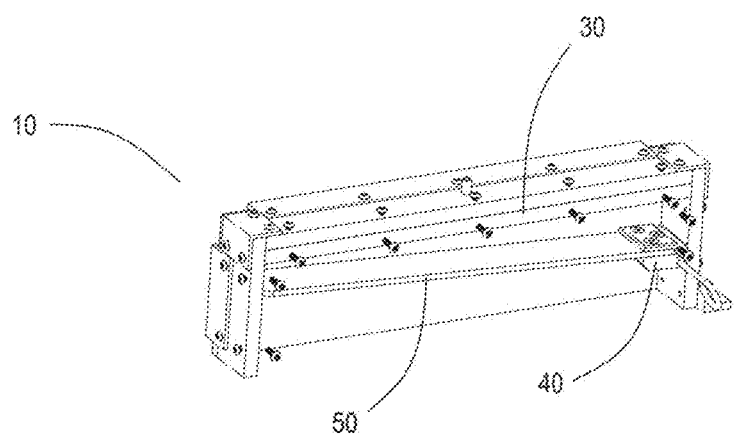
FIG. 3A shows a perspective view of a molding rig embodiment, a subassembly of an embodiment of an apparatus for thermally reforming a thermoplastic article.
Figure 3B:
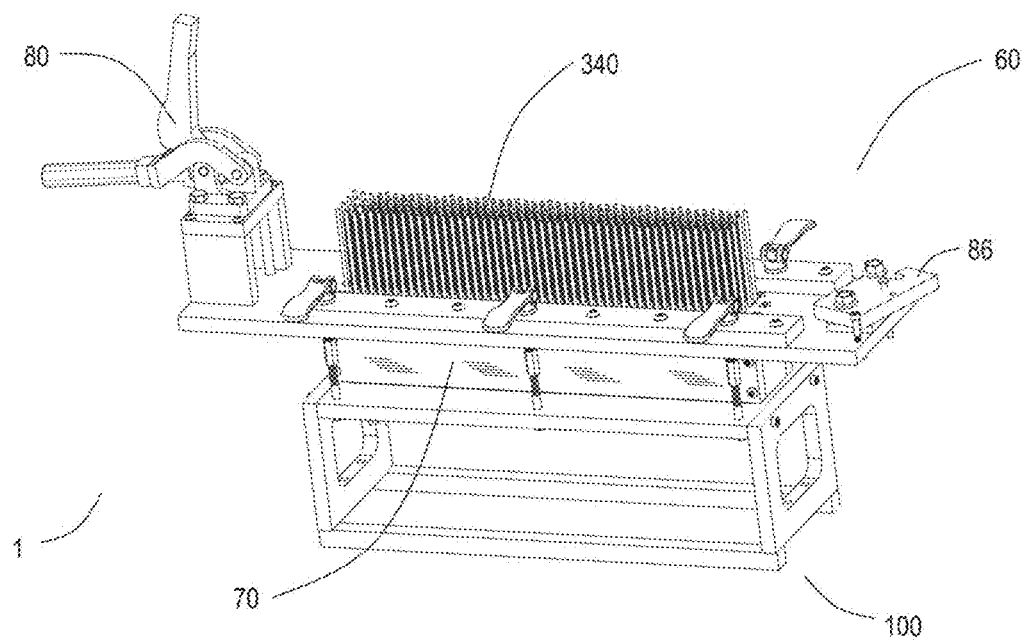
FIG. 3B shows perspective view of an embodiment of a reconfigurable pin tool, a subassembly of an apparatus for thermally reforming a thermoplastic article, used in conjunction with the molding rig embodiment of FIG. 3A.

Referring now to FIG. 2B, pin plate top 64 and pin plate bottom 65 serve as a central structure for reconfigurable pin tool 60 and contour reforming apparatus 1 as a whole. Pins 340 are now visible (with molding rig 10 removed); they reside within pressurizable container 70 and extend below it, and they extend above it into molding rig 60 when it is installed. One or more securing elements secure the attachment of reconfigurable pin tool 60 and a pressurizable container 70 (FIG. 3B) to reconfigurable pin tool 60. These securing elements may include a clamp assembly 80 and a locking element 86. Clamp assembly 80 is disposed on top and at one end of the pin plate top 64. Clamp assembly 80 is arranged such that it can exert pressure on molding rig. 10. In one embodiment, locking element 86 takes the form of a swivel lock, and is disposed at the end of pin plate top 64 opposite the clamp assembly 80. These various approaches to securing and clamping are provided merely as illustrative examples; the scope of the technology includes any suitable arrangement of these or functionally similar elements.

Figure 5A:
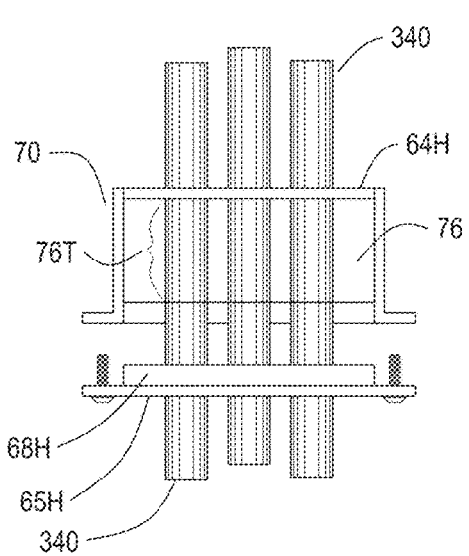
FIGS. 5A-5C show detail views of a segment of a reconfigurable pin tool, showing views of pins through plates and as immersed and stabilized within a silicon bed.
Figure 5B:
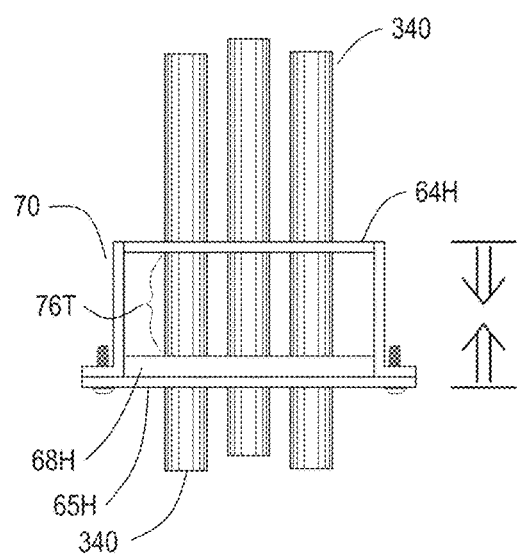
Figure 5C:
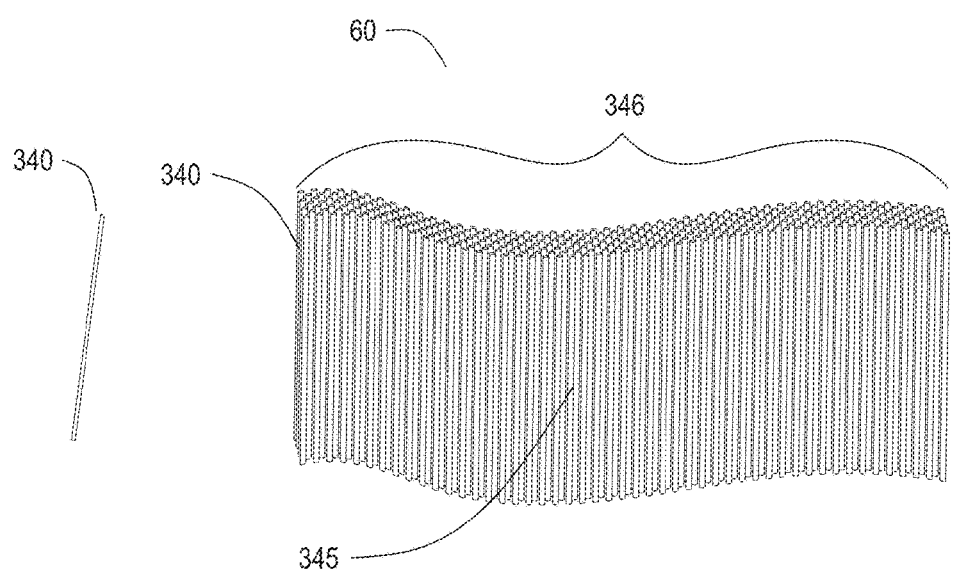

It may be advantageous for pins 340 (FIG. 3B) to not move completely freely. A level of resistance to movement may provide a useful stability to pins in the pin field 345 (FIG. 5C). It may be further advantageous for the resistance to movement to be variable or controllable. The scope of the technology includes any mechanism or arrangement that can stabilize pins in a pin field and in a controlled and modulated manner, allow them to move, and restabilize in a desired position. One particular embodiment of a pin movement resistance mechanism will now be described in some detail.

Pin movement resistance mechanism 70 is disposed below the pin plate top 64 of reconfigurable pin tool 60, and supported therefrom. In some embodiments, pin resistance mechanism 70 is a pressurizable container that includes side plates 72 (FIG. 2B) and end plates 74 (FIG. 4), and is filled with a pool 76 of silicone or any suitable elastomer. Referring to FIGS. 4, 5A, and 5B, pins 340 are vertically aligned; each pin is aligned through a series of pass-through elements that penetrate (from top to bottom) through holes in pin plate top 64 and the pusher plate 68, and as a tunnel 76T through elastomeric pool 76.

Pin movement resistance mechanism or pressurizable container 70 can be put into a pressurized state by use of cam clamps 62 and pull rods 63, which collectively pull up the pusher plate against the top plate, thus applying pressure on elastomeric pool 76 contained therein. The pins, even when pressurizable container 70 is not under pressure, may be held vertically stable by at least some friction as they pass through holes (64H, 68H), and they are further vertically held in place by the viscosity of the elastomeric pool 76. ("Vertical" is used to describe the alignment of movement since that is appropriate for this particular embodiment of reconfigurable pin tool 60. In alternative embodiments, the pins need not be vertically aligned.) As the elastomer in pressurizable container 70 comes under pressure, several consequences may ensue. Inventors theorize that even though silicone is considered to be an incompressible fluid, in fact, some compression may occur, possibly by way of compression of trapped air. Further, by virtue of pressure, the viscosity of silicone may increase. Both of these factors would increase the static friction between the surface of the pins and the silicone in which they are immersed, such increased friction providing resistance to movement of the pins through the silicone.

The embodiment of a contour replicating apparatus 1 and its components, as shown in considerable detail FIGS. 1-6 and FIGS. 8-11, can be understood in broader terms. For example, reconfigurable pin tool 60 can be understood as that portion of the device that supports pins 340 or actuatable rods in a neutral position, is able to move them or allow their movement to a position wherein the pin field, as a whole, creates a desired contour, and can secure pins within the field to an extent that the pin field 345 is stable against pressure when used as a molding surface. Molding rig 10 can be understood as any structure that brings the reconfigurable surface of a pin tool and a target article to be reformed or reshaped together in a controlled way, securing the target article in its original form, and allowing the release of the article in a stable reformed shape after a molding engagement.

Further, the reconfigurable pin tool 60 in the embodiment shown in FIGS. 1-6, and in FIGS. 8-11 has a pin field that is operated or actuated by a software-driven CNC machine 200; thus in this actuation sense, pins 340 can be regarded as passive. In other embodiments, however, pins may be self-actuated, as for example by small, networked motors (e.g., servomotors or stepper motors) that are collectively driven by a software program.

As noted, in alternative embodiments, a pin field housed in a device or apparatus could be oriented in any direction other than verticality. Further, whereas in the presently described embodiment, the pin field is horizontal and flat at the outset of methods, as described below, the pin field and its associated actuatable molding surface need not be flat, and the article to be molded need not be flat at the outset, in its original configuration. Articles and molding surfaces, merely by way of example, could have contoured initial shapes, and include cavities and openings.

As shown in FIGS. 5A-5B, in another aspect of pin movement, resistance may be created by friction between the pins as they move through holes, such as holes through pin plate top 64H and the pusher plate 68H. In alternative embodiments, mechanisms that control lateral pressure between pins and the pinholes in a clamping manner may be used to vary or control resistance of pin movement.

FIGS. 5A-5B show detail views of pins 340 in a pin movement resistance mechanism 70, which in this embodiment is a pressurizable container filled with a pool of elastomer 76. In some embodiments, the elastomer is silicone. FIG. 5A shows the pressurizable container 70 as being detached from pusher plate 68H in an exploded view. FIG. 5B shows the pressurizable container bolted to pusher plate 68H and under pressure (as indicated by arrows). When pressurizable container 70 is in an unpressurized condition, pins 340 can slide up and down with relative freedom; when container 70 is pressurized, pins 340 are resistant to being moved. As mentioned above, each pin 340 is aligned through a series of pass-through elements that penetrate (from top to bottom) through pin plate top 64H and the pusher plate 68H, and as a tunnel 76T through elastomeric pool 76. A "tunnel", in this sense, is not a fixed structure, but rather a void within the elastomeric pool that is formed when pins are first inserted into the pool, pushing away the elastomer.

FIG. 5C shows a detail view of the reconfigurable pin tool device 60 that clarifies distinctions between the individual pins 340, the pin field as a whole 345, and molding surface 346 that, in this embodiment, is formed by the upper surfaces of pins 340 throughout the entire pin field 345. More generally, the upper surface of pin field 345 represents an actuated or actuatable surface that can be useful in a forming or molding operation, but may have applications broader than molding, per se. For example, a controllably contoured surface may be useful as a quality control device for checking contoured articles. In the exemplary embodiments provided herein, the actuatable surface is used to mold malleable thermoplastic materials. In this or other, alternative embodiments, it could also be used to mold or shape other materials, such as thermoset materials, sheet metal, settable building materials, ceramics, or foods. In another example, an actuatable surface could be used in an injection mold. In general, such an actuatable surface may be useful when a contoured surface, engineered with high resolution is needed, but a durable contoured article is not needed or cost effective, and one in which fine-tuning of shape is advantageous.

Figure 6:
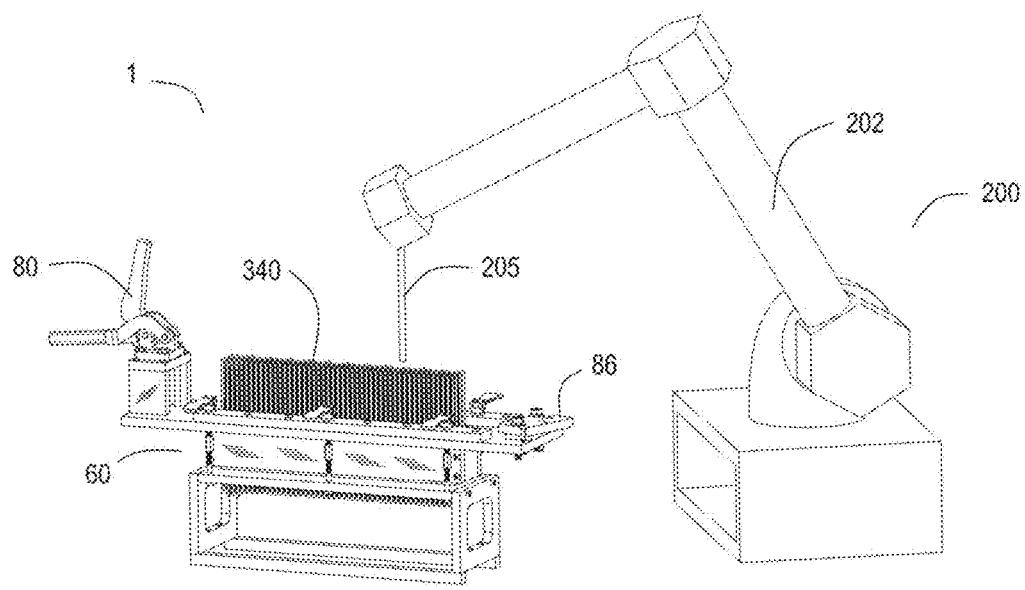
FIG. 6 shows a schematic rendering of a CNC machine with a robotic arm that is poised to manipulate pins in an embodiment of a thermal reforming apparatus.

FIG. 6 shows a schematic rendering of a CNC machine 200 with a robotic arm 202 that has a distal actuator peg 205 poised to manipulate the thermal reforming apparatus 1. This is merely a schematic representation of CNC machine 200 and its operation in a fabrication facility. In practice, CNC machines are typically highly automated, and may further operate cooperatively with other automated machines and robots that may be fixed in position or independently mobile.

Figure 7A:
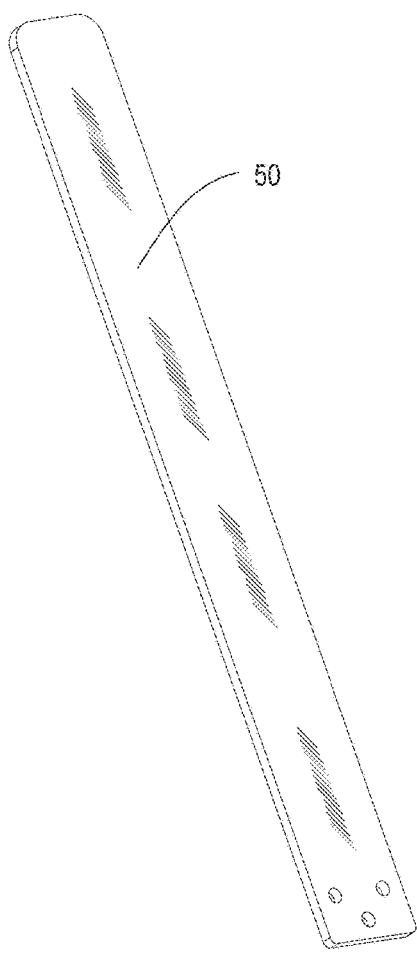
FIG. 7A shows a thermoplastic fiber composite strut for a prosthetic socket in neutral form, such as one that would be included in an inventory of components from which an individually-fitted prosthetic socket could be assembled.
Figure 7B:
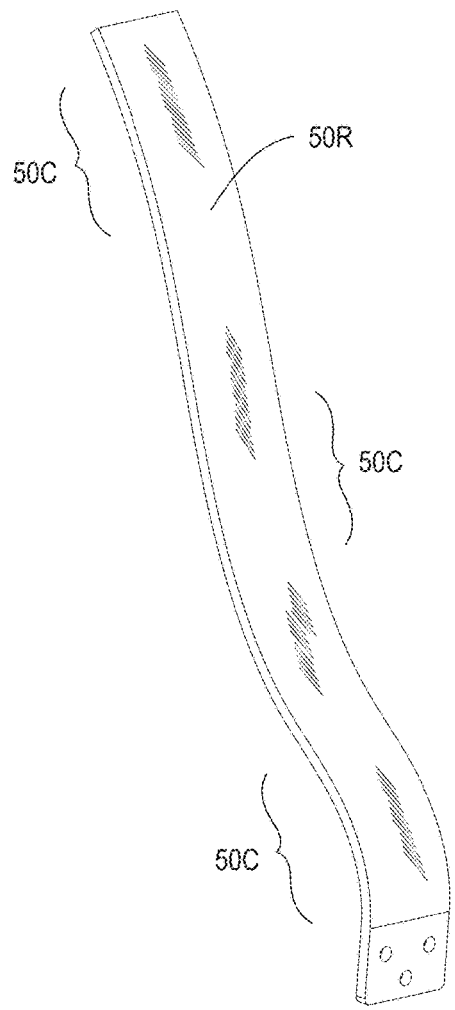
FIG. 7B shows the thermoplastic fiber composite strut seen in FIG. 7A after a thermal reforming process, as performed by an embodiment of the thermal reforming apparatus described herein, the thermal reforming process rendering the neutral form into a form that replicates the contours associated with a longitudinally aligned domain on the surface of a residual limb.

FIGS. 7A-7B shows an example of a thermoplastic article before and after having been thermally reformed by an embodiment of an apparatus as described herein. The exemplary article is a thermoplastic fiber composite strut 50, a component of a modular prosthetic socket as described in U.S. patent application Ser. No. 14/213,788. Accordingly, FIG. 7A shows a thermoplastic fiber composite strut 50 in an original form, and FIG. 7B shows strut 50R in a reshaped form after a thermal reforming event, per embodiments of the invention, that has contoured the strut to replicate the contours associated with a longitudinally aligned domain on the surface of a residual limb. Sites of reformed curvature or contouring are shown in regions 50C.

Thermoplastic fiber composite struts (U.S. patent application Ser. No. 14/213,788) typically include fiber in a continuous or substantially continuous form. In particular embodiments, substantially all of the fiber included in the thermoplastic composition is in a substantially continuous form. Such continuous fiber form imparts strength and stiffness to the strut and allows thermal reforming within the strut. In practice, thermoplastic fiber composite struts 50 are cut from flat stock sheets of thermoplastic fiber composition, and reforming into an appropriate shape is a step in the assembly of a complete modular prosthetic socket. Inasmuch as struts in their initial form are flat, some embodiments of a method of assembling a prosthetic socket include thermally reforming all struts.

Figure 21:
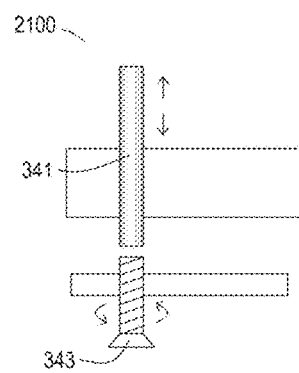
FIG. 21 shows an embodiment of a mechanism for moving a pin in which a pin embodiment is positioned proximate a screw.
Figure 22:
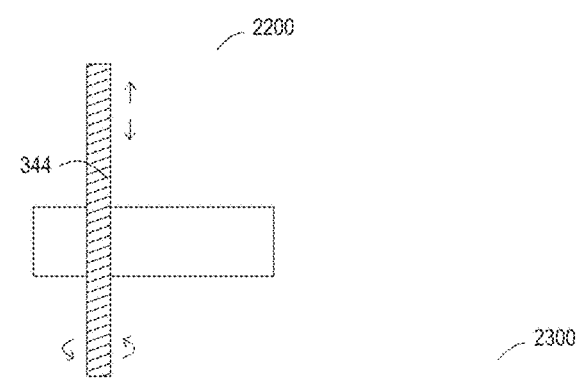
FIG. 22 shows a shows an embodiment of a mechanism for moving a pin that is in the form of a screw or threaded rod.

FIGS. 8-11 show side views of an apparatus for thermally reforming a thermoplastic article 50 at various stages during a method of operating the apparatus during a thermal reforming process. In some embodiments, movement of elements within the apparatus are passive, in that all the power driving movement of pins 340 is provided by manipulation of pins by CNC machine 200. In other embodiments of the invention, as shown in FIGS. 21-22, pins 340 can be self-driven, individually, by dedicated actuators such as small motors.

Figure 8:
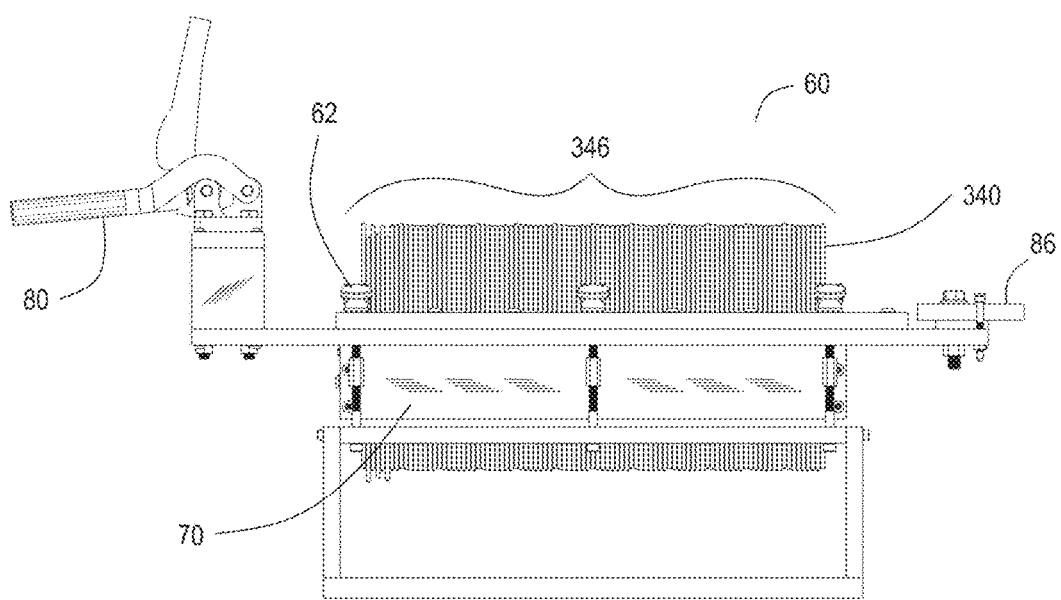
FIGS. 8-11 are side views of embodiments of an apparatus for thermally reforming a thermoplastic article so as to conform to a desired profile, the apparatus being driven by a computer numeric control (CNC) machine, and the figures illustrating a method of using the apparatus.
Figure 9:
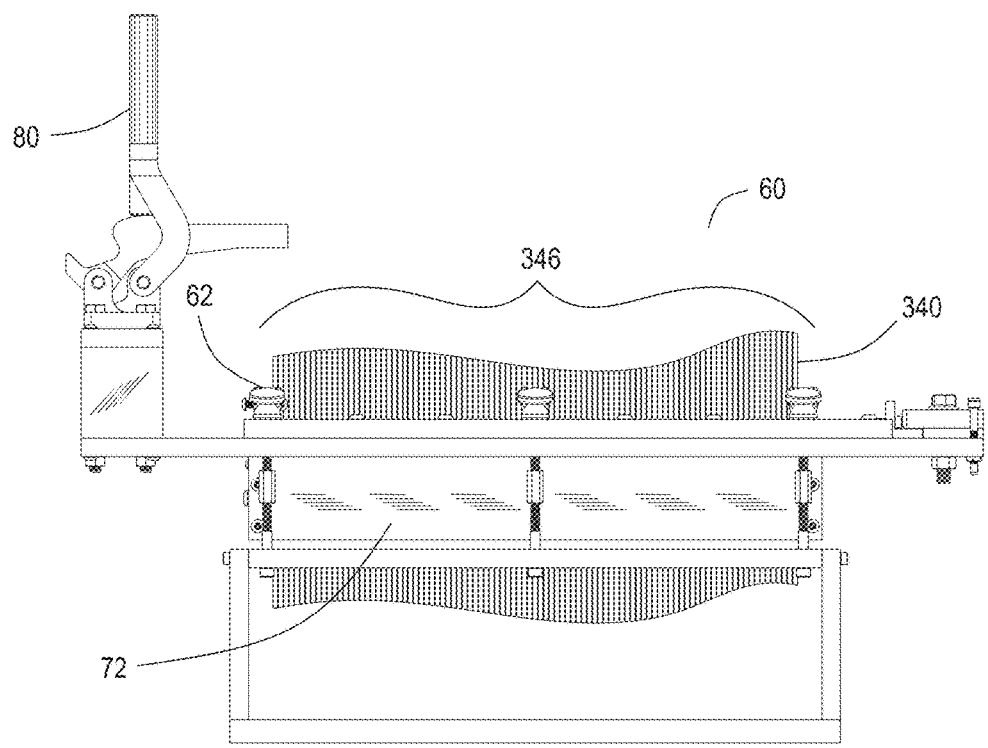
Figure 10:
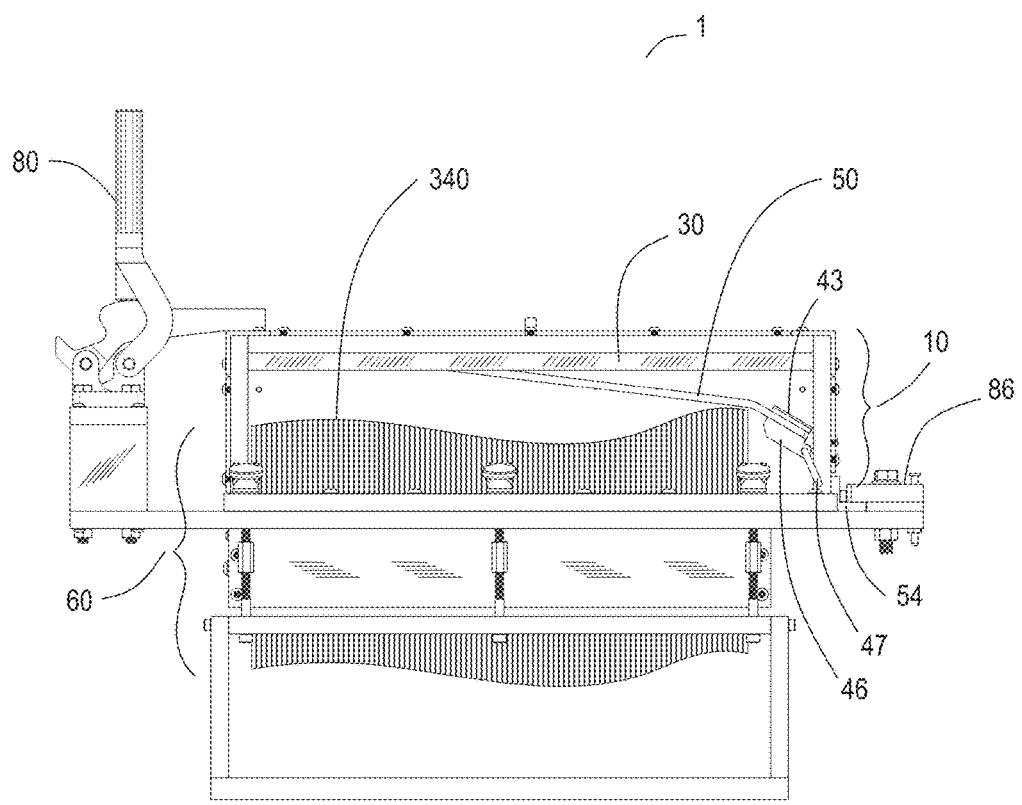
Figure 11:
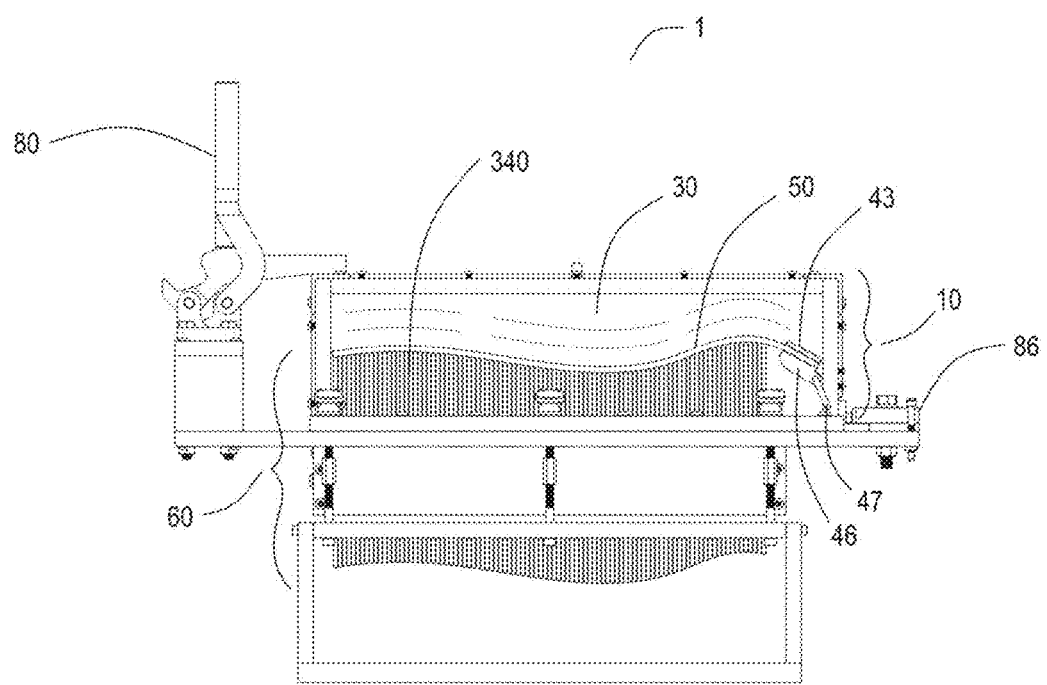

FIGS. 8-9 show thermal reforming apparatus 1 without molding rig 10 installed on top of reconfigurable pin tool 60; in FIGS. 10-11, molding rig 10 is installed on top of reconfigurable pin tool 60. FIG. 8 shows the reconfigurable pin tool 60 prior to CNC machine 200 actuation of pins 340. Typically, at the outset of a reforming process, pins 340 that collectively form a pin field 345 are lined up, all at approximately the same height; the upper surface of pin field 345 constitutes a reconfigurable molding bed or molding surface 346. As shown in FIG. 8, molding bed 346 is flat. In practice, this can be accomplished by manually leveling the pins from below by applying a board or any suitable flat surface upward against their lower ends. FIG. 9 shows the reconfigurable pin tool 10 [Add 10 as a label in FIG. 8. Same comment as above.] after CNC machine 200 has actuated pins 340. Actuation, in this context, refers to pressing down each pin 340, individually, to a desired height or elevation with respect to the field 345 of pins 340 as a whole.

FIG. 10 shows an assembled apparatus 1 for thermally reforming a thermoplastic article, a molding rig 10 now placed on top of the reconfigurable pin tool 60. A heated thermoplastic article such as a prosthetic socket strut 50 is in place within molding rig 10; this view is prior to downward application of pressure to strut 50 by the pressure bladder 30.

FIG. 11 shows the assembled apparatus 1 as in FIG. 7 after expansion of the pressure bladder 30, which is now expanded downward against the raised pins 340.

The various steps illustrated by the operation of the reconfigurable pin tool apparatus 1 are outlined more specifically in the form of method embodiments in FIGS. 12-15, as described below.

Embodiments of the technology may include a pin field 345 of any size appropriate for an article to be thermally reformed, and pins within the pin field 345 may vary in terms of length, width, and cross sectional shape. Further, the density of pins within the pin field can vary to be appropriate for the article being reformed. Pin density can be expressed as number of pins/pin field area, as well as the total percentage of the pin field area that is occupied by a pin (in contrast to the void space between pins).

In one example, a pin field 345 includes pins 340 equally spaced apart in a hexagonal pattern such that the center of each pin is 0.293 inches distant from each nearest neighboring pin. The pin field is arranged with 7 pins in a row arranged across the width, and a length that includes 49 rows. In this example, pins with a circular cross sectional profile have a diameter of 0.125 inches are distributed at a density of 14 pins/square inch. Pins of this diameter and distribution density thus occupy about 17.2% of the total surface area of the pin field.

As described, a pin resistance mechanism 70 in the form of pressurizable container can be pressurized so as to stabilize vertical movement of pins 340 within the pin field. In one example, when the pressurizable container is pressurized, each pin is stable when up to 15 lbs. pressure is applied to it. If, as in this example, the pin field has a pin density of 14-pins/square inch, the pin field thus resists movement unless pressure of at least about 210-lbs./square inch is applied to it.

The example of a contour replicating apparatus 1, as shown in FIGS. 1-6 and 8-11, has an arrangement in which a thermally malleable strut is being reformed by pressing the strut between a deliberately or affirmatively shaped molding surface 346 and a compliant pressing surface (bladder 30). In this example, all of the information related to a desired contour is associated with, or has been conveyed to, the contoured pin field; the compliant pressing surface carries no specific contouring information.

In alternative embodiments, both surfaces pressing against the malleable strut may be an affirmatively contoured pin field. In these embodiments, the strut is sandwiched between two opposing pin fields, each pin field set up by an operation of a CNC machine. The profiles of the pin fields may be exactly complementary, or they may vary to a small but significant degree. In a case in which the pin fields vary from being complementary, the variance can manifest in the form of varying thickness or surface features along the length of the thermoplastic article being reformed.

In other alternative embodiments, rather than being actuated by a CNC machine, pins 340 in a pin field 345 may be actuated by pneumatic or hydraulic mechanisms, or small motors. In other embodiments, the actuatable elements need not be pins. Instead, and merely by way of example, the actuatable elements could be closely spaced cables, individually sheathed so as to provide independent movement. In other alternative embodiments, the facets forming the reconfigurable surface, rather than being the surfaces of actuatable pins, may be panel-type surfaces significantly larger than the diameter of a pin or actuatable element. In some instances, this panel surfaces may be supported by more than one actuatable element.

Some of these alternative embodiments of a reconfigurable pin tool apparatus are shown in FIGS. 18A-35, and as described further below.

Figure 12:
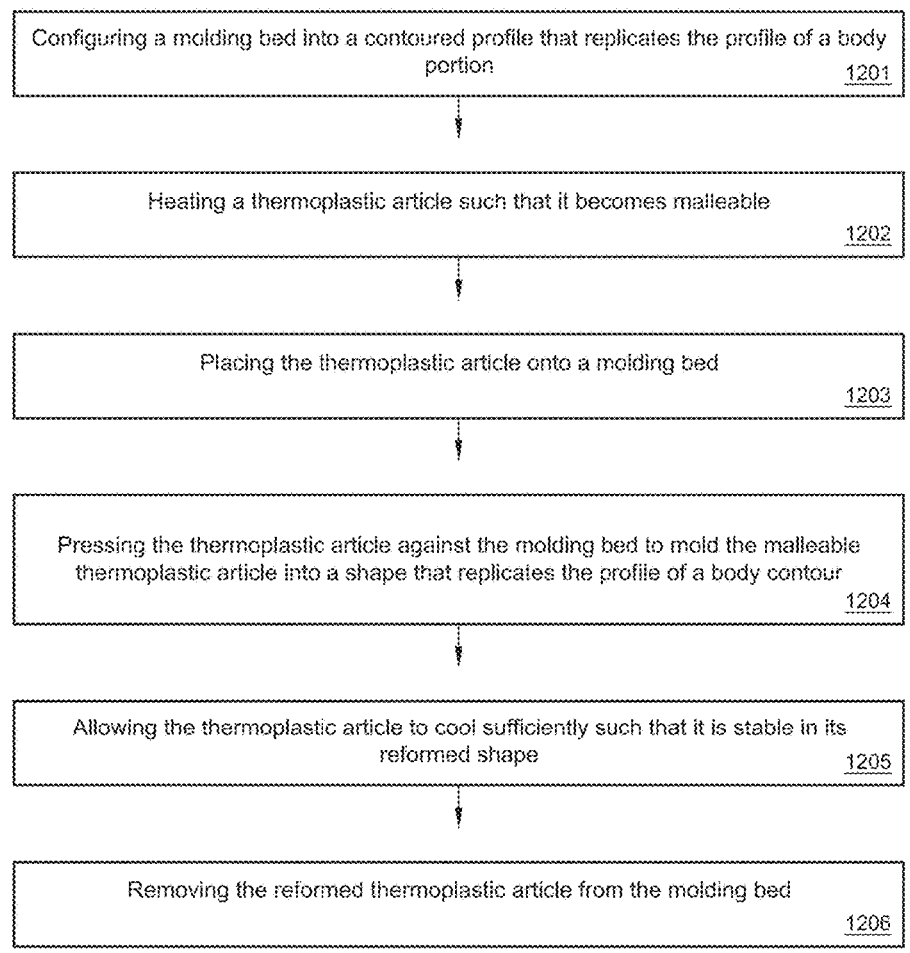
FIG. 12 is a flow diagram of an embodiment of a method of thermally reforming a thermoplastic article to assume a desired shape.

FIG. 12 is a flow diagram of a method of thermally reforming a thermoplastic article to assume a desired shape. In a particular embodiment, the method applies to thermally reforming a thermoplastic fiber composite strut to take the form (or the complement to the form) of a portion of a residual limb. Accordingly, in one embodiment, a method for thermally reforming a thermoplastic article, such as a thermoplastic fiber composite strut, particularly one in which fiber is in a continuous or substantially continuous form, may include the following steps:

Step 1201 Configuring a molding bed into a contoured profile that replicates the profile of a body portion Step 1202 Heating a thermoplastic article such that it becomes malleable Step 1203 Placing the thermoplastic article onto the molding bed Step 1204 Pressing the thermoplastic article against the molding bed to mold the malleable thermoplastic article into a shape that replicates the profile of a body contour Step 1205 Allowing the thermoplastic article to cool sufficiently such that it is stable in its reformed shape Step 1206 Removing the reformed thermoplastic article from the molding bed Embodiments of the method shown in FIG. 12 may be performed by embodiments of reconfigurable pin tool apparatus 1 as provided herein and shown in FIGS. 1-6 and 8-11, as well as alternative reconfigurable pin tool embodiments, as shown in FIGS. 18A-35.

Figure 13:
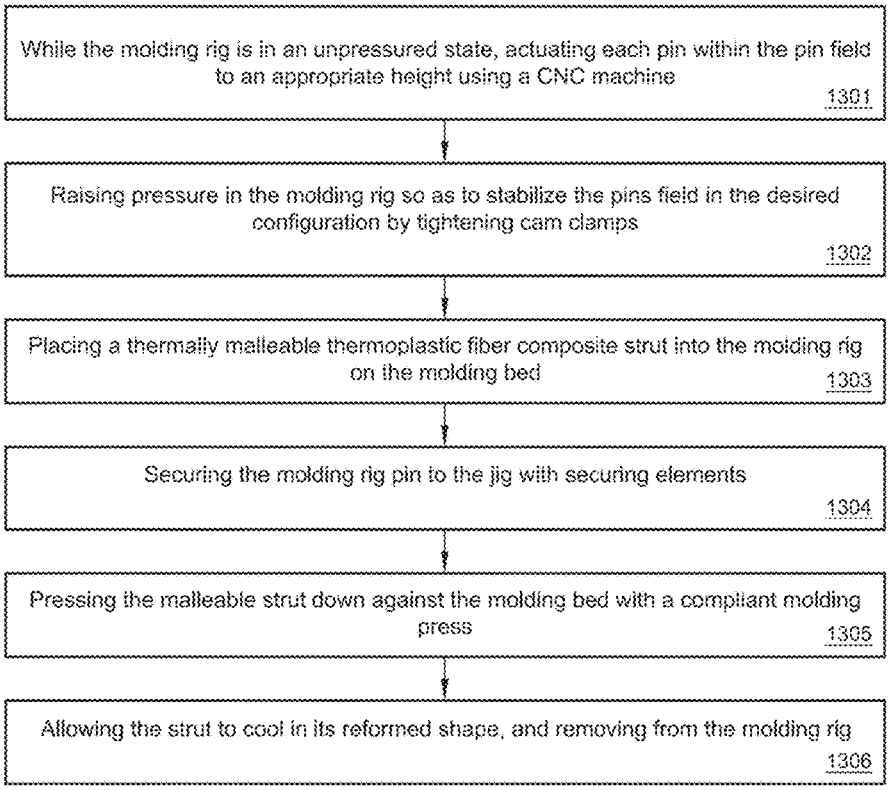
FIG. 13 is a flow diagram of an embodiment of a method of operating an apparatus to thermally reform a thermoplastic-fiber composite strut to complement a portion of a residual limb.

FIG. 13 is a flow diagram of a method of operating an apparatus to thermally reform a thermoplastic-fiber composite strut to complement a portion of a residual limb. This method is similar to the method shown in FIG. 12, but is particularly adapted as a method for operating a thermal reforming apparatus (FIGS. 1-6) as it moves through various operational stages (FIGS. 8-11) to reform a thermoplastic article (FIGS. 7A-7B).

In one embodiment, this method may include the following steps:

Step 1301 While the molding rig is in an unpressurized state, actuating each pin within the pin field to an appropriate height using a CNC machine.

Step 1302 Raising pressure in the molding rig by tightening cam clamps. The increased pressure within the elastomer pool or bed in the molding rig increases the viscosity of the elastomer sufficiently such that the pins are vertically stabilized in place.

Step 1303 Placing a thermally malleable thermoplastic article into the molding rig above the pin field.

Step 1304 Securing reconfigurable pin tool to the molding rig.

Step 1305 Pressing the malleable strut down against the top surface of the pin field, thereby reforming it so as to assume a desired contour. Pressing may occur by way of inflating a compliant molding press, such as an inflatable bladder.

Step 1306 Allowing the strut to cool in its reformed shape, and removing it from the molding rig.

As introduced above, the technology provided herein relates to a system and methods of operating the system to acquire digital knowledge of a body part and ultimately translate that knowledge into the production of a highly individualized product. An example of such a system and method, as provided herein, relates to acquiring digital knowledge of a patient's residual limb, and using that digital knowledge to fabricate components of a modular prosthetic socket. The technology delivers a prosthetic socket component whose contouring reflects that of the patient's residual limb. More importantly, the technology delivers a prosthetic socket as whole, as assembled from such components, which is biomechanically and medically appropriate for the individual patient.

Examples of prosthetic sockets that include thermoplastic fiber composite struts as a central structural feature are described in U.S. Pat. No. 8,978,224 and U.S. Pat. No. 9,044,349, as well as U.S. patent application Ser. No. 14/213,788. Prosthetic sockets and component struts are but one example of the application of provided technology to digitally fitting an article to a patient. More generally, this example represents a subset of other medical devices and components, and other wearable articles that can be fabricated by embodiments of method as shown in FIG. 14.

Figure 14:
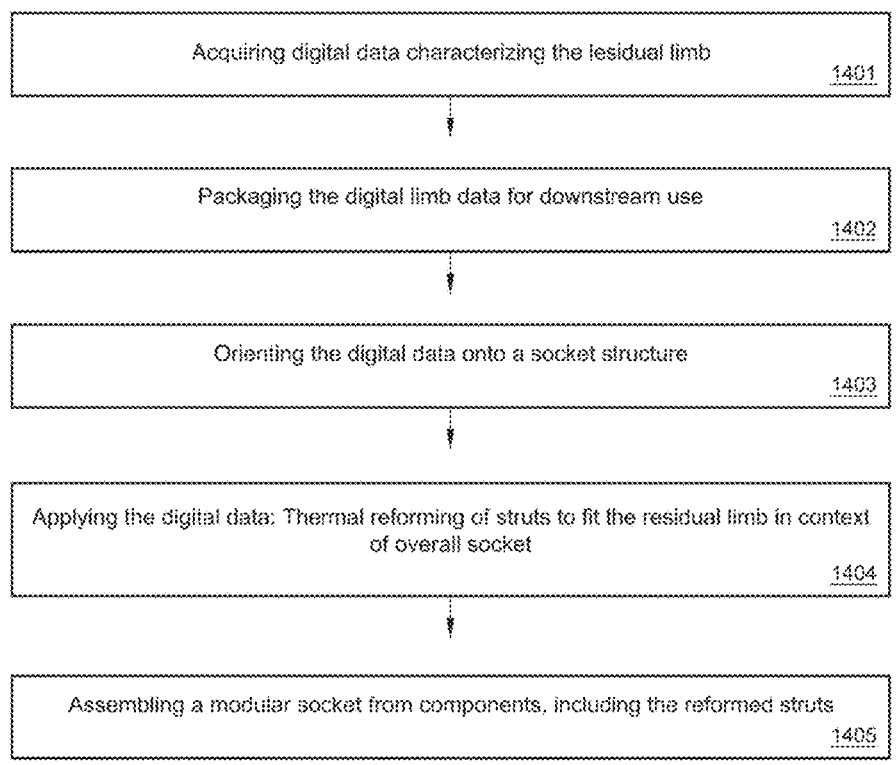
FIG. 14 is a flow diagram an embodiment of a method of digitally fitting a modular prosthetic socket to a patient's residual limb.

FIG. 14 is a flow diagram of a method of digitally fitting a modular prosthetic socket to a patient's residual limb. More particularly, the diagram shows the flow of information related to a profile of a residual limb from a method of its acquisition through to the point of translation into a modular prosthetic socket that appropriately fits the residual limb.

In one embodiment, this method may include the following steps:

Step 1401 Acquiring digital data characterizing the residual limb.

Step 1402 Packaging the digital limb data for downstream use.

Step 1403 Orienting the digital data onto a socket structure.

Step 1404 Applying the digital data: thermal reforming of struts to fit the residual limb in context of overall prosthetic socket.

Step 1405 Assembling a modular socket from components, including the reformed struts.

Figure 15:
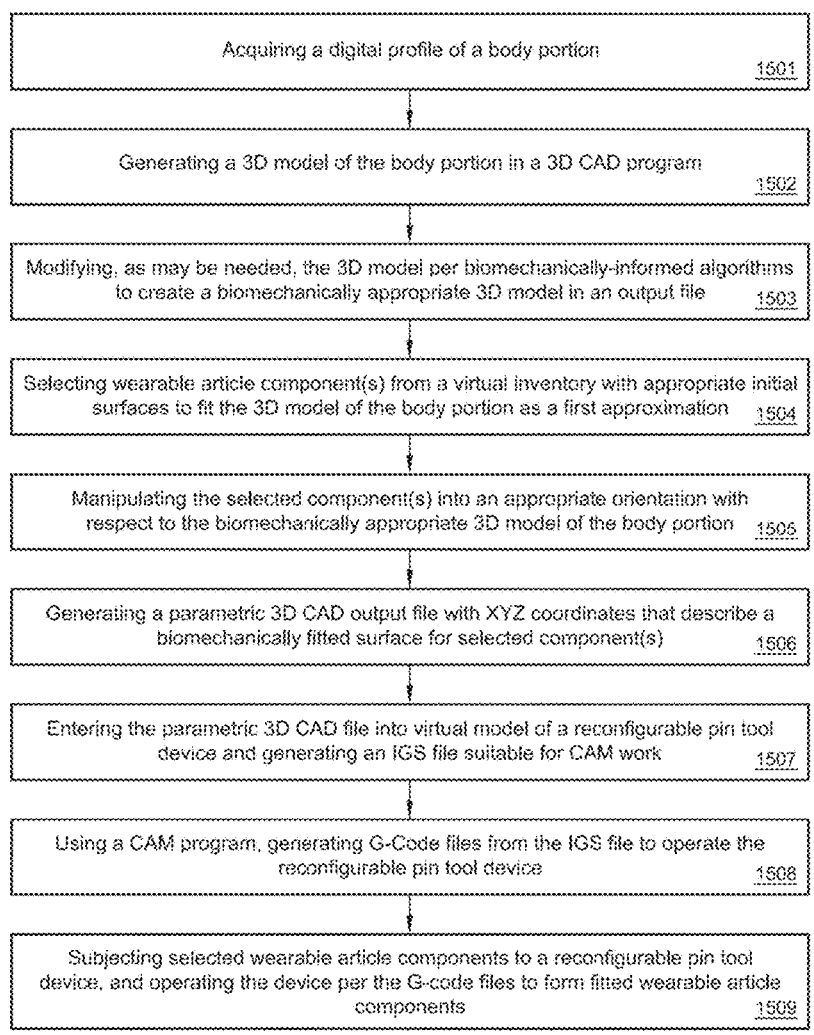
FIG. 15 is a flow diagram of a method of fabricating a custom-fitted wearable article.

Each of these steps will now be described in greater detail. Step 1401 relates to acquiring digital data that characterizes the residual limb. Acquiring such data may occur by any suitable approach, including any one or more of scanning, photographing, casting, mapping with a three-dimensional point reference device a three-dimensional digital or physical representation of the residual limb, or by manual measurement. It is advantageous to map the residual limb so as to have digital data informative of the overall shape of the residual limb at a surface level. It is further advantageous to have digital data informative of the tissue underlying the surface, data that can differentiate among hard tissue, such as bone, dense tissue such as muscle, and soft tissue such as fat. Accordingly, in one embodiment, the method relates to acquiring spatial and compliance data from a fitting sock having one or more populations of sensors. Such sensor populations may include positional sensors and acoustic sensors as described elsewhere and as shown in FIGS. 15A-16.

Step 1402 relates to integrating the raw data acquired in Step 1401 into a 3-dimensional profile of the residual limb, including tissue density information, and packaging the digital limb data for downstream processing and implementation. Raw positional and compliance data derived from Step 1401 are processed by way of fitting algorithms into a data package appropriate for downstream processing. Data packaging algorithms are flexible enough to process data from common sources other than a fitting sock embodiment as provided herein, such common sources including any one or more of scanning, photographing, casting, X-ray, ultrasound, MRI, CT scanning, mapping with a three-dimensional point reference device a three-dimensional digital or physical representation of the residual limb, manual measurements or any methodology that provides profiling data that is sufficient for the purposes described herein. Packaging the data derived from the fitting sock may include the application of algorithms based on considerations related to tissue compliance in addition to overall size and shape of the residual limb. Algorithms may apply clinical or biomechanically appropriate consideration input.

Step 1403 relates to orienting or registering the digital profile of a residual limb into a prosthetic socket structure. For example, modular prosthetic socket components, such as a strut, need to conform to a particular region of the residual limb after they are assembled together with other prosthetic socket components to create a complete socket. The digital data package from Step 1402 are registered or oriented onto a socket structure that is selected from possible optional configurations. Optional socket structures, per available prosthetic socket components (as may be found in an inventory of components that vary in size and/or shape) and available configuration options, may be chosen by algorithmic approaches and/or by operator input. Based on a preferred socket configuration, specific parts in component inventories are selected for inclusion in a group of socket components that would provide the best initial approximation of a good fit with the residual limb. Packaged residual limb profile data may then be applied to defining desired contours of each strut, as it is appropriately oriented onto a virtual model of the residual limb by software. Digital fitting data files then need to be made suitable for a CNC machine, so that the CNC machine can operate a reconfigurable pin tool apparatus.

Step 1404 relates to applying the digital data to a thermal reforming of struts to fit the residual limb in context of overall socket. Computer numerical control (CNC) machine processes convert digital fitting data files into operational instructions for the setting up the contour replicating apparatus. The thermal reforming method includes heating the struts, placing them in the reconfigurable pin tool, pressuring heated struts against a reconfigurable pin tool profile that replicates contours of the residual limb into contours of the strut.

Step 1405 relates to assembling a modular socket from components, including the reformed struts. A modular socket is assembled from a variety of components held in inventories that include the individual components in various sizes and shapes. When components such as struts have been reformed to a shape that conforms to the shape of a residual limb, they are then used in the assembly of a prosthetic socket custom-fitted to a particular individual patient. Each strut can be said to fit the residual limb, but fit, in its fullest sense, is derived from the combination of the totality of the fitted individual components.

FIG. 15 is a flow diagram of a method of fabricating a custom-fitted wearable article or device. More particularly, the diagram shows the flow of information related to a profile of a body portion from its acquisition through to the point of translation into a wearable device or article custom-fitted to an individual patient or subject. The method embodiment shown in FIG. 15 is consistent with the method embodiment of FIG. 14, but includes further detail on the handling of digital profile data through a series of data file transformations, as performed by various CAD programs with particular capabilities.

In one embodiment, this method may include the following steps:

Step 1501 Acquiring a digital profile of a body portion.

Step 1502 Generating a 3D model of the body portion in a CAD program.

Step 1503 Modifying, as may be needed, the 3D model per biomechanically-informed algorithms to create a biomechanically appropriate 3D model in an output file (e.g., an STL file).

Step 1504 Selecting wearable article component(s) from a virtual inventory with appropriate initial surfaces to fit the 3D model of the body portion as a first approximation.

Step 1505 Manipulating the selected component(s) into an appropriate orientation with respect to the biomechanically appropriate 3D model of the body portion.

Step 1506 Generating a parametric 3D CAD output file with XYZ coordinates that describe a biomechanically fitted surface for selected component(s).

Step 1507 Entering the parametric 3D CAD output file into virtual model of a reconfigurable pin tool device and generating a second IGS file suitable for CAM work.

Step 1508 Using a CAM program, generating G-Code files from the second IGS file to operate the reconfigurable pin tool device.

Step 1509 Subjecting selected wearable article components to a reconfigurable pin tool device, and operating the device per the G-code files to form fitted wearable article components.

More than one 3D CAD software program may be used in executing this method embodiment, although in particular embodiments, a single all encompassing program can be envisioned that handles all steps. Different steps, however, do require particular capabilities.

For example, it is advantageous for steps 1502 and 1503 to be handled by a CAD program that is adapted to handle specific features that are characteristic of the final product. In some embodiments, for example, it is advantageous for a CAD program executing these steps to be adapted for prosthetic products, their structure, componentry, and the features of residual limbs to which the prosthetic products are intended to fit. Canfit™ from Vorum (Vancouver, BC, Canada) is a contemporary example of a suitable program, among others, that can provide equivalent or similar functionality.

Steps 1508 and 1509 require a computer-aided manufacturing (CAM) program, i.e., software designed to control machine tools and related machinery in the manufacturing of work pieces. A contemporary example is InventorCAM™, but any functionally equivalent or more advanced program is suitable and included in the scope of the invention. Reconfigurable pin tools, as referred to in Step 1509, can make use of any of the reconfigurable pin tools described herein, including those shown in FIGS. 18A-35, and as described herein.

Embodiments of the technology include variations on the method embodiment shown in FIG. 15, and in some embodiments of the method, steps may be added, or steps may be skipped. In one variation, for example, rather than starting with a digital profile of a residual limb, the starting object is a positive plaster cast of the residual limb, or a negative mold from which a positive cast can be produced. Once the plaster cast is captured digitally, the various steps described in FIG. 15 are similar or substantially identical. In another variation, the plaster cast can be physically modified prior to digitally profiling it, and thereafter, appropriate steps in FIG. 15 are similar or substantially identical.

Embodiments of the provided technology include a mapping device for acquiring a digital profile of an anatomical region. Such an anatomical profile includes the overall external form factor of the region, and my further include a map of tissue compliance that registers with the external form. Tissue compliance is a function of underlying anatomy that differentiates tissue based on density and/or hardness. Accordingly, the profile, as a whole, captures external and internal anatomy. The example provided herein that demonstrates the utility of the technology is a fitting sock that fits over a residual limb. The scope of the technology, however, is not limited to this particular embodiment. A fitting garment need not be sock shaped, and the anatomical portion need not be a residual limb. The portion of the anatomy may be any body portion, intact or partially intact. The fitting garment can be sized and shaped to accommodate any such anatomical portion or feature. Further still, for the purposes of acquiring a digital profile of a residual limb or any body portion, embodiments of the mapping device provided herein represent but one example of a device and method for acquiring such a digital profile.

Figure 16A:
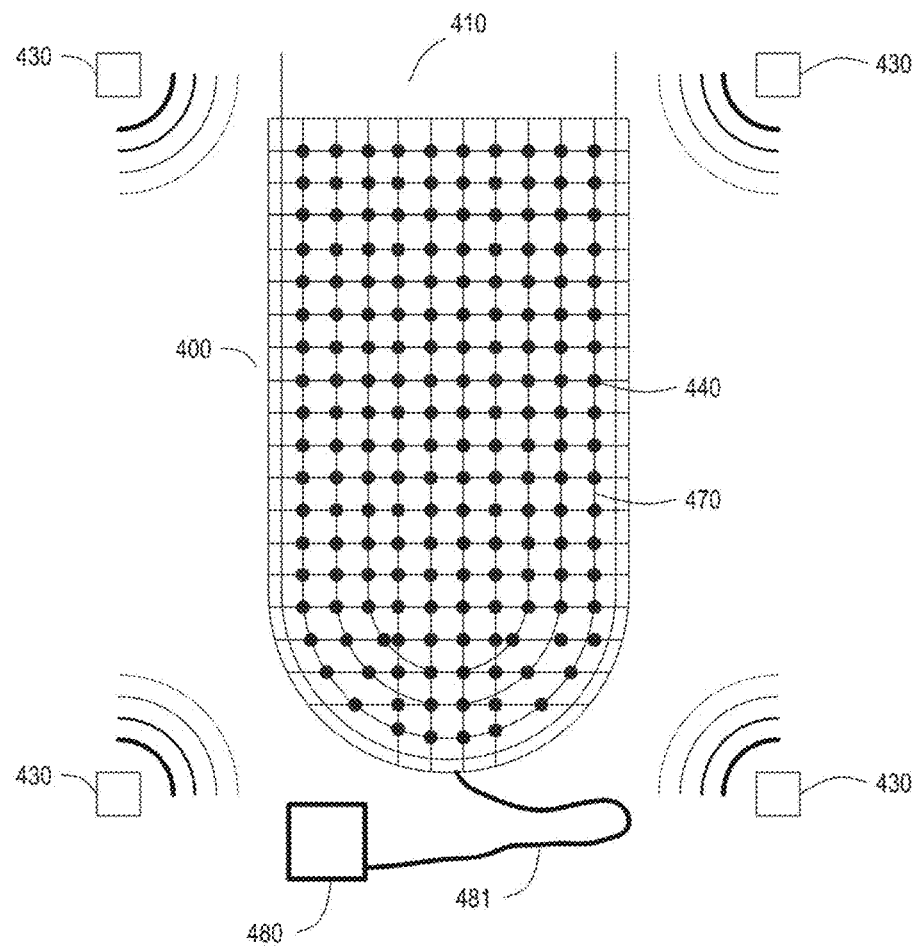
FIG. 16A shows an embodiment of a digital fitting sock that captures an external profile of a residual limb and a map of underlying compliance that is reflective of local tissue density.
Figure 16B:
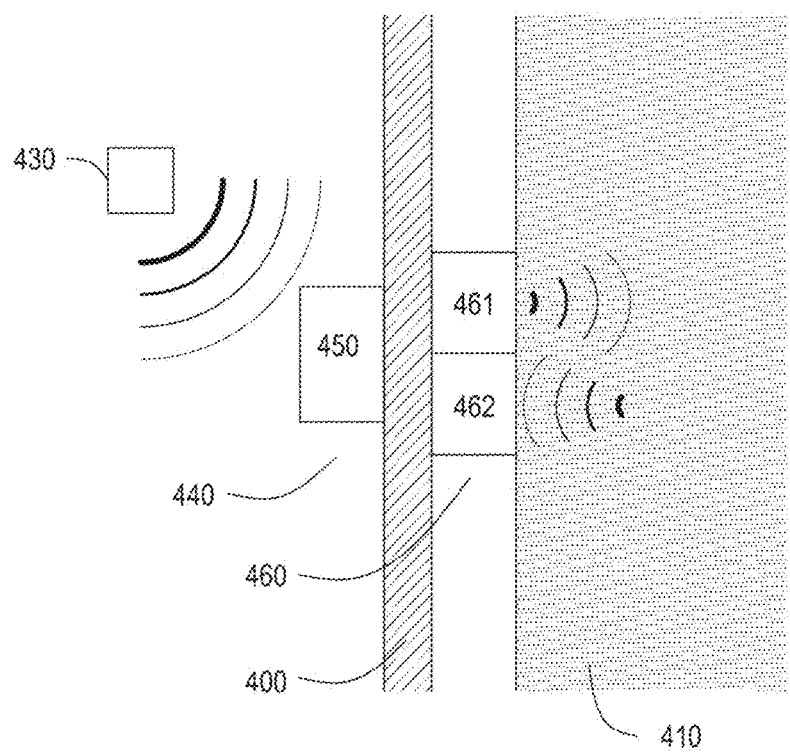
FIG. 16B shows a cross-sectional profile detail of the digital fitting sock of FIG. 16A.

FIG. 16A shows an embodiment of a mapping device in the form of a digital fitting sock 400 that captures an external profile of a residual limb and a map of underlying compliance that is reflective of local tissue density. FIG. 16B shows a cross sectional profile detail of the digital fitting sock of FIG. 16B. Embodiments of a compliant or elastic fitting sock 400 include multiple sensor assemblies 450 that are connected together by a wired network 470, the wired network being in electronic communication with a computer 480 by way of connection 481 Multiple radiofrequency (RF) or sonar emitters 430 are arranged external to the fitting sock 400. Typically, four or more external emitters are used in a system that supports the operation of the fitting sock 400.

In the embodiment shown in FIGS. 16A and 16B, the sensor assemblies 440 include at least two types of sensors: (1) radiofrequency (RF) or sonar receivers 450 configured to receive signals from external emitter sources, and (2) acoustic compliance sensors 460. As seen in FIG. 16B, radiofrequency (RF) or acoustic sensors (according to whether external emitters are transmitting RF or sonar frequencies) are positioned on the external surface of digital fitting sock 400. Acoustic or "compliance" sensor assemblies 460 are positioned on the internal surface of fitting sock 400, and include a transmitter unit 461 and a receiver unit 462. The details of the positioning of RF or acoustic sensors 450 on the external surface of digital fitting sock and the positioning of acoustic compliance sensor assemblies 440 on the internal surface of digital fitting sock 400 are particular to this exemplary embodiment, and may be different but functionally equivalent in alternative embodiments. Further, the arrangement of a single wired network serving sensors 450 and 440 is particular to this exemplary embodiment; other functionally equivalent or suitable arrangements could be made in alternative embodiments.

Positional mapping of the surface confirmation of digital fitting sock 400 creates an informative profile of the size and shape of a residual limb enclosed by the digital fitting sock. External triangulated emitters emit signature signals that differ either in frequency or in signal emission pattern so that receivers 450 can individually identify each emitter 430. The intensity of a signal emission from each emitter 430 decreases as a function of the distance between the emitter and the receiver; thus intensity of the signal, as received, is a measure of distance. When distance values between a single receiver and each of multiple emitters are received and processed, the position of the receiver relative to the emitters can be determined.

Signal data, as received by each receiver 450 from each emitter 430 are conveyed to computer 480 by way of wired network 470 and connector 481. Software in the computer captures all signal data, and can determine the distance of each receiver 450 from each emitter 430 and assign it a unique spatial position, and accordingly determine the position of each receiver 450 relative to every other receiver 450. By this approach, a 3-dimensional model of the digital fitting sock, and by extension, the residual limb contained within the sock, can be assembled.

A biomechanically appropriate prosthetic socket provides a substantially conformal fit over a residual limb, but considerations other than strict conformal congruence are also important. For example, some degree of overall compression of the residual limb may be advantageous, to provide a good grasp of the limb and counter edema that can occur. Compression may be understood or quantified by considering the nominal circumference of a naked residual limb and the nominal inner circumference of a prosthetic socket, or more particularly, the nominal inner circumference of the space within a prosthetic socket liner, within a prosthetic socket. It is common, by way of example, for the relevant inner circumference of the socket or socket liner to be about 5% less than the circumference of the residual limb. However, particularly in the case of prosthetic socket with struts and open spaces, it is important that compression not be applied to circumferential sites on the residual limb where bone structure is close to the surface. More generally, it is advantageous to have a map of internal structure within the residual limb that is informative regarding tissue density. In broad generality, it is appropriate to press into soft compressible tissue (e.g., fat or muscle), and it is inappropriate to press into bone.

The function of the acoustic compliance sensors is to map distribution of tissue density within the 3-dimensional structure as determined by the positional sensors. The compliance sensors both emit and receive acoustic signals. The outgoing signal has a known frequency and amplitude profile; as the signal penetrates tissue, some of the energy is absorbed, and some of it is reflected back toward the source. The frequency and/or amplitude of transmitted acoustic energy may cycle through predetermined ranges. Energy reflected by tissue returns with a lag in the frequency phase that is associated with tissue density. Hard tissue reflects energy back quickly; the phase lag is relatively small. Soft tissue reflects energy back more slowly; the phase lag is relatively large. By this approach, phase lag of bounced back signal is informative with regard to nearby tissue density. This information, when registered on the 3-dimensional profile, as provided by positional sensors, provides a detailed map of tissue density within the 3-dimensional model of the residual limb.

Figure 17:
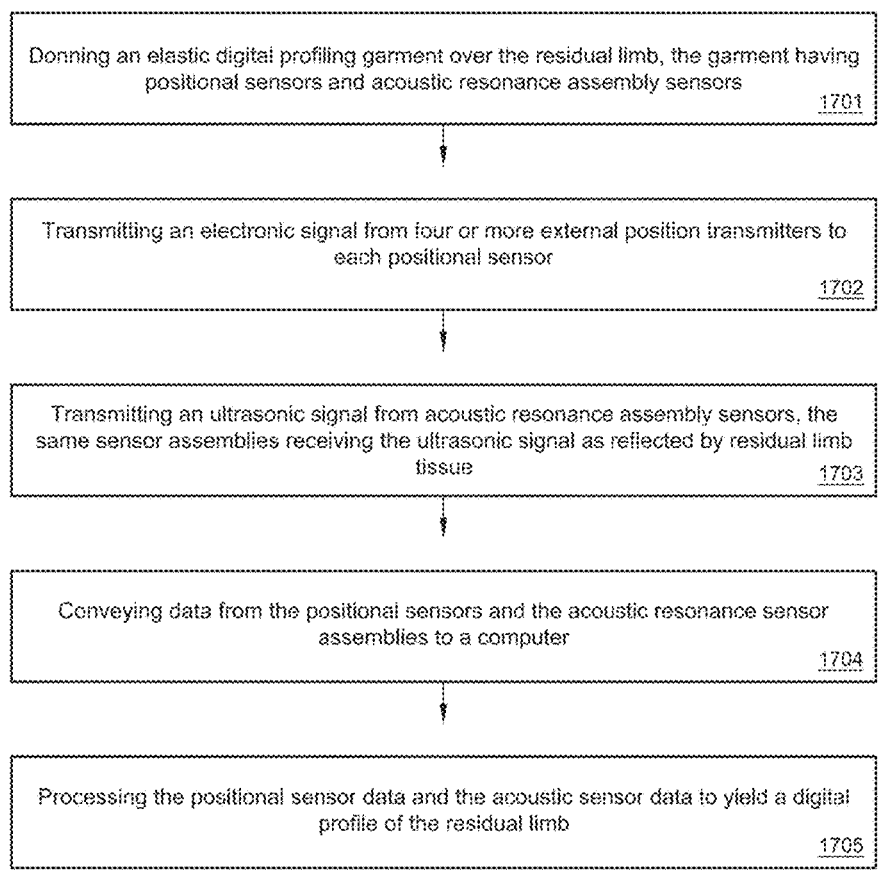
FIG. 17 is a flow diagram of a method for digitally profiling a residual limb.

FIG. 17 is a flow diagram of a method for digitally profiling a residual limb. More particularly, the diagram shows the acquisition of digital data by a device and system as shown in FIGS. 16A and 16B, and as described above. In one embodiment, the method shown in FIG. 17 may include the following steps:

Step 1701 Donning an elastic digital profiling garment over the residual limb, the garment having positional sensors and acoustic resonance assembly sensors Step 1702 Transmitting an electronic signal from four or more external position transmitters to each positional sensor Step 1703 Transmitting an ultrasonic signal from acoustic resonance assembly sensors, the same sensor assemblies receiving the ultrasonic signal as reflected by residual limb tissue Step 1704 Conveying data from the positional sensors and the acoustic resonance sensor assemblies to a computer Step 1705 Processing the positional sensor data and the acoustic sensor data to yield a digital profile of the residual limb Aspects of the disclosed technology relate to an apparatus for thermally reforming a thermoplastic article toward a desired shape, such desired shape conforming to or being complementary to a portion of a body. The technology further relates to the an aspect of the process whereby the body portion is captured in digital form, and that digital knowledge being used toward the end of guiding the thermal reforming, such that the reformed article does assume the desired form. Exemplary embodiments described herein relate particularly to capturing a digital profile of a residual limb of an amputee patient, and using that digital knowledge to inform the contouring a thermoplastic-fiber composite strut that will be used in the assembly of a modular prosthetic socket. These embodiments, however, are not limiting with regard to the scope of the invention. Various embodiments may be usefully applied toward fabrication and individualization of a broad range of devices that interface with a portion of the body and engage in contact, and in absorbing and distributing pressure. Such devices, by way of example non-limiting examples, may include orthotics, exoskeletal device interfaces, body braces, pillows, and body support devices such as wheel chairs, walkers, and the like.

Embodiments of reconfigurable pin tool apparatus, as described above and shown in FIGS. 1-6 and 8-11 are capable of thermally reforming articles along a single surface. In the context of reforming a narrow target article (such as a prosthetic socket strut) this is effectively remolding a contour within a single plane. The single plane, as defined by an adjustably contoured molding bed (FIGS. 5C, and 9-11) includes the line representing the longitudinal axis of a thermoplastic strut. When multiple struts are being reformed by an embodiment of the reconfigurable pin tool apparatus prior to assembly into a socket, each strut is typically handled one at a time. (The exception would be if two struts were being reformed, side-by-side, to assume the same reformed profile.) An assembled socket that includes multiple such thermally reformed struts represents a structural configuration that can be considered thermally reformed or reshaped circumferentially around the central longitudinal axis of the socket.

Figure 18A:
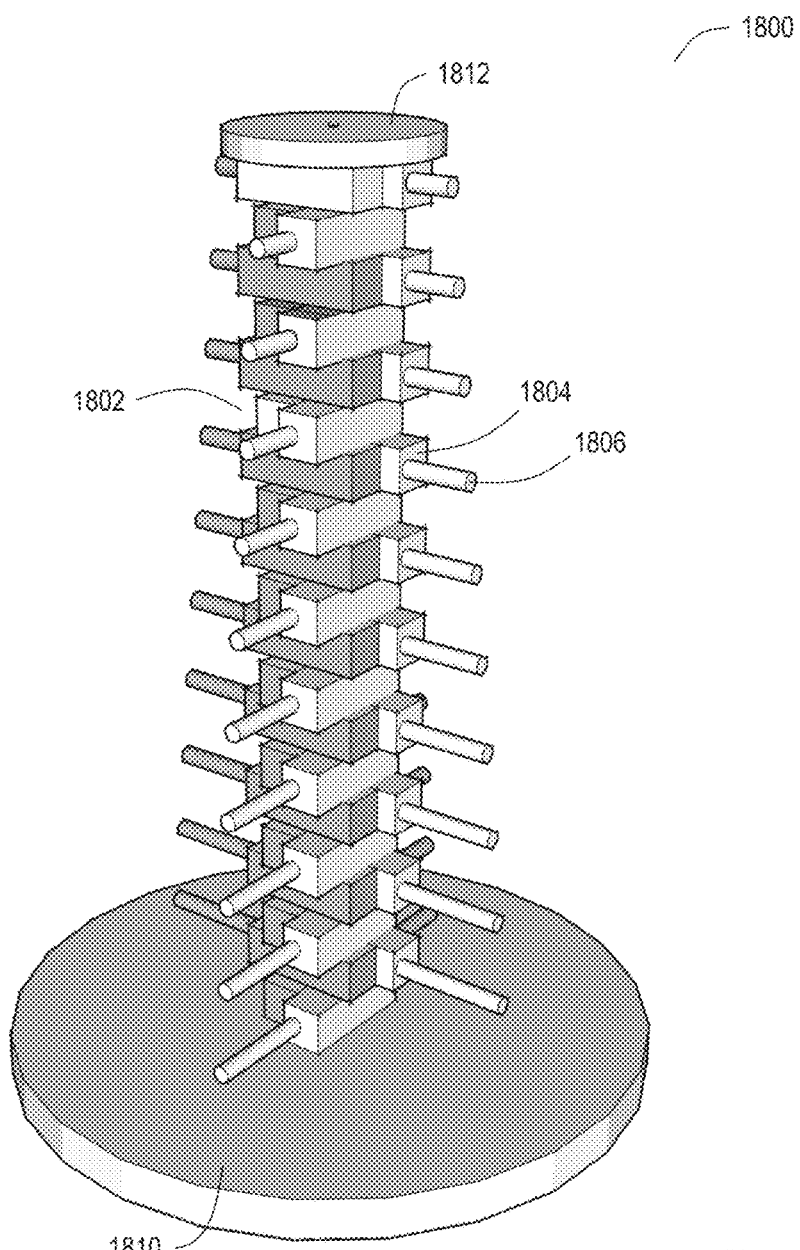
FIGS. 18A-18C show an embodiment of a circumferentially operable reconfigurable pin tool apparatus of Type A, with actuated rods extending outward from a central tower toward the periphery.
Figure 18B:
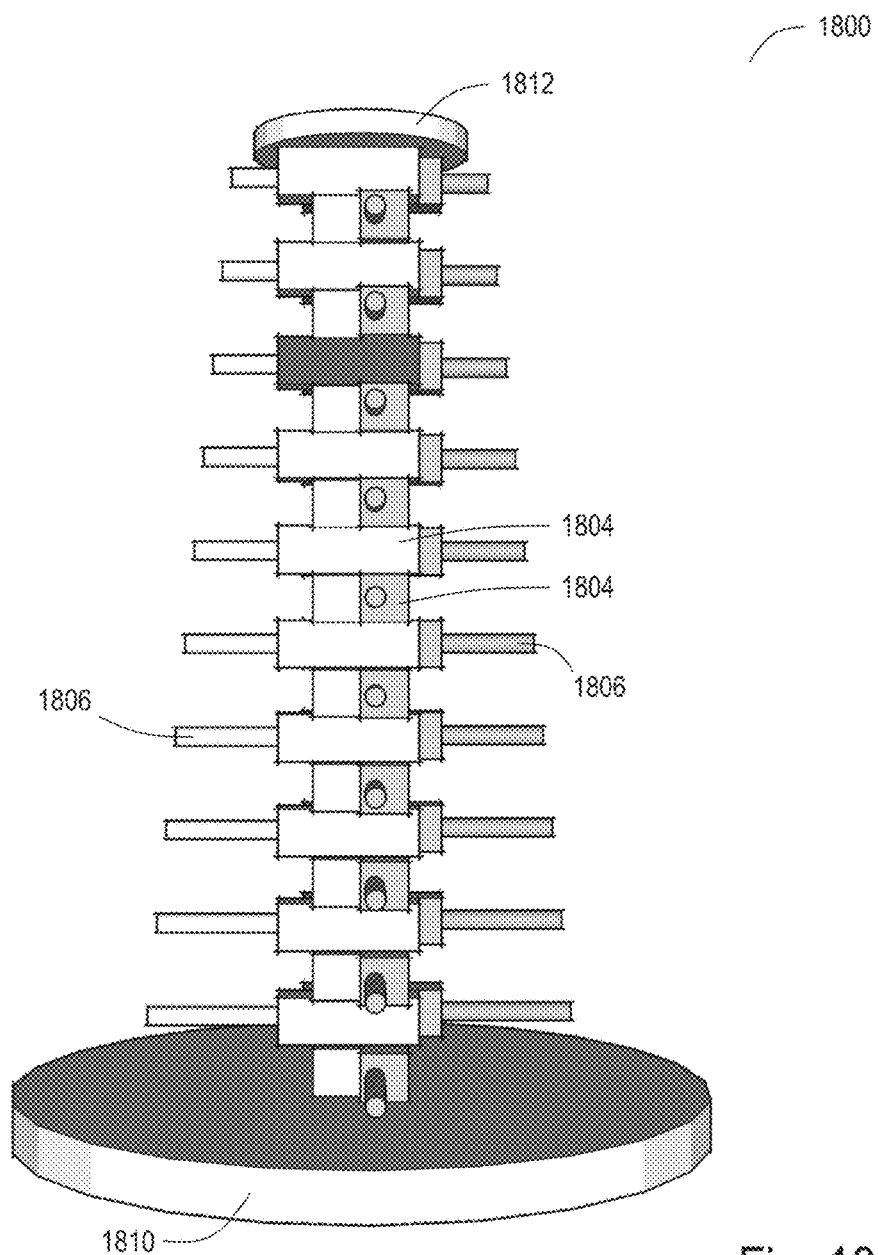
Figure 18C:
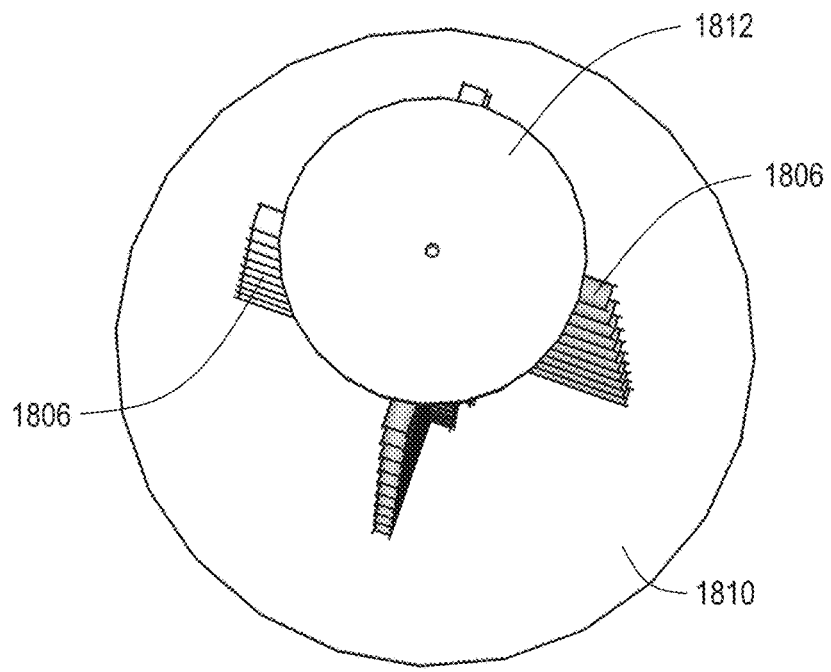

Turning now to other embodiments of the invention that are capable of thermally reforming an article, or multiple articles, in a circumferential configuration simultaneously: Type A circumferential embodiments are shown in FIGS. 18A-18C), and Type B circumferential embodiments are shown in FIGS. 19A-19F. If the width of the target surface to be reformed is sufficiently wide and if the molding surface has sufficient resolution, then molding can occur effectively in two planes. Regardless of whether each molding surface is reforming a target surface in 1-plane or 2-planes, the combined effect of molding multiple target articles simultaneously that are destined to be assembled together represents a 3D reforming or reconfiguration. Embodiments of a reconfigurable pin tool of this 3D arrangement (Type A and Type B) effectively form one or more reforming beds, each bed being capable of reforming a target surface of a thermoplastic article.

In one example (3D or circumferential reforming embodiment Type A), as shown in FIGS. 18A-18C, an apparatus operates by moving an array of plates outward from a central position against an adaptive or compliant surface to achieve a desired external form. The molding surface created or defined by the reconfigurable pins is a positive model or positive mold of the residual limb against which target reformable articles are pressed against from their internal surface. This first approach can be likened to the mechanism of an adjustable fitting mannequin. In this Type A embodiment arrangement, the reformable target article (such as a strut) are pressed outwardly against a substantially consistent resistance, such as an elastic wrapping or compliant enclosure.

In a second example for a 3D or circumferential reforming embodiment (Type B), as shown in FIGS. 19A-19F, an apparatus operates by moving an array of pins inward from a peripheral position against a centrally-situated adaptive or compliant surface to achieve a desired internal form. The molding surface created or defined by the reconfigurable pins is a complementary model or negative mold of the residual limb, against which target reformable articles are pressed from their external surface. This second approach, wherein a molding form is created by pins impinging on a centrally positioned target article, can be caricaturized as being similar to the mechanism of an iron maiden. In this Type B arrangement, the reformable target articles (such as a strut) are pressed against a compliant or adaptive central object, such as neutral shaped inflatable bladder.

Circumferential reconfigurable pin tool devices such as Type A and Type B may be directed toward a method of thermally reforming a thermoplastic article to assume a desired shape (FIG. 12), a method of digitally fitting a modular prosthetic socket to a patient's residual limb (FIG. 14), and/or a method of fabricating a custom-fitted wearable device (FIG. 15).

FIGS. 18A-18C show a circumferentially operable reconfigurable pin tool 1800 of Type A, with actuated pins or rods 1806 extending outward from a central tower 1802. FIG. 18A shows a low angle top perspective view of the circumferentially operable device 1800; FIG. 18B shows a side view of the device 1800; and FIG. 18C shows a steep angle top perspective view of the device 1800. Circumferential pin tool device 1800 includes central tower 1802, positioned vertically on a base plate 1810 and culminating at the opposite end in a top plate 1812. Central tower 1802 is formed from stacked actuator units 1804. Each actuator unit 1804 hosts an actuating rod 1806, typically enabled by a motor (not shown) that can move the rod 1806 in (toward a central position) and out (toward a peripherally extended position) under the control of an electronic network. In this embodiment of the circumferential pin tool device 1800, the actuator units 1804 are paired, the rods 1806 extending from each single unit 1804 of the pair in opposite directions. In this particular embodiment, each paired unit is oriented perpendicularly with respect to its immediate upper and immediate lower neighbor.

Accordingly, in this configuration, the actuator units 1804 are oriented in an X-axis/Y-axis manner, with rods 1806 extending in four directions from the center of central tower 1802. This configuration would be appropriate, for example, to simultaneously reform four thermoplastic fiber composite struts for a modular prosthetic socket, as described in U.S. Pat. No. 8,978,224 and in U.S. patent application Ser. No. 14/213,788, both of which are incorporated into this present application in their entirety.

While circumferential pin tool embodiment 1800 has four outwardly projecting spoke-like pin sets, spaced apart at equal angles of 90 degrees, alternative embodiments may include any other suitable number and configuration of units 1804. For example, actuator units 1804 need not necessarily be paired; accordingly actuator units could host rods or pins that emanate from the center in the form of three spokes or five spokes. If actuator units are paired, as they are in embodiment 1800, they could be arranged such that they emanate from the center in a six-spoke configuration.

Figure 30A:
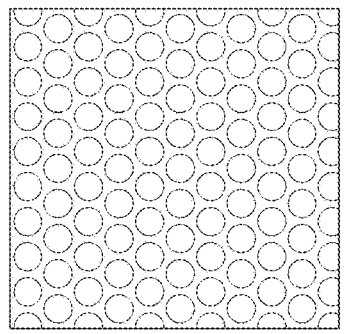
FIG. 30A shows an array of pins having a round cross sectional profile.
Figure 30B:
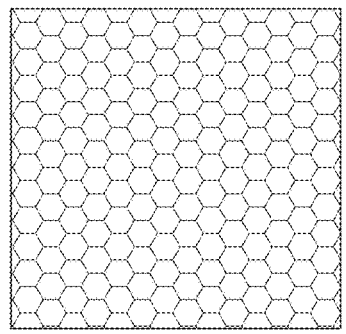
FIG. 30B shows an array of pins having a hexagonal cross sectional profile.
Figure 30C:
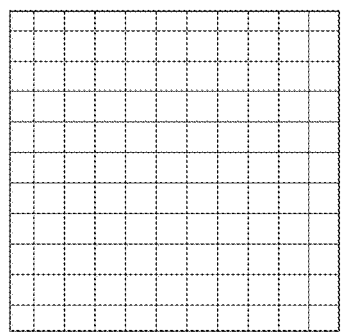
FIG. 30C shows an array of pins having a square cross sectional profile.
Figure 32:
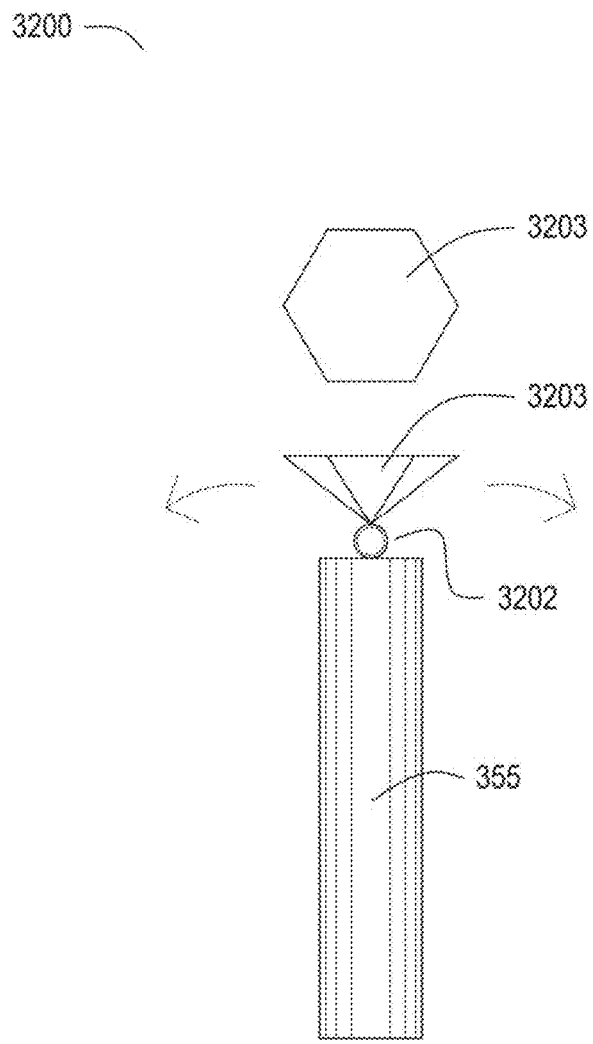
FIG. 32 shows an embodiment of a pin in which a hexagonal engaging element is attached to the molding engagement end of a pin by way of a gimbal.

Additionally, although rods 1806 are shown as round in cross section, the cross-sectional profile can assume many variable forms, a few of which are shown in FIGS. 30A-30C. Still further, the outwardly projecting end of each rod 1806 can be embellished or altered, such that it differs from the cross sectional profile of the rod 1806 as a whole. By way of example, a plate or panel arranged to be orthogonal to the rod could be positioned at the outward end. In another example, a panel could be supported by a gimbal mechanism, as shown in FIG. 32. The effect of having a broadened surface or panel at the external end of a rod 1806 is to allow the engagement of a larger surface area of a target article to be reformed from the pressure delivered by an individual pin.

As noted above, circumferential pin tool device 1800 operates by moving an array of rods or plates (attached to rod) outward from a central position against an adaptive or compliant surface to achieve a desired external form. Reformable target articles are positioned against the external ends of rods 1806 or associated panels, and the target article (a strut, for example) is engaged on it internal surface, and pressed outward against the compliant surface or constraint. In one example, a compliant constraint can be applied around the articles being reformed by an elastic wrapping, as provided, for example, by a wrapped length of an Ace bandage, or an enveloping donut-shaped inflatable bladder.

Figure 19A:
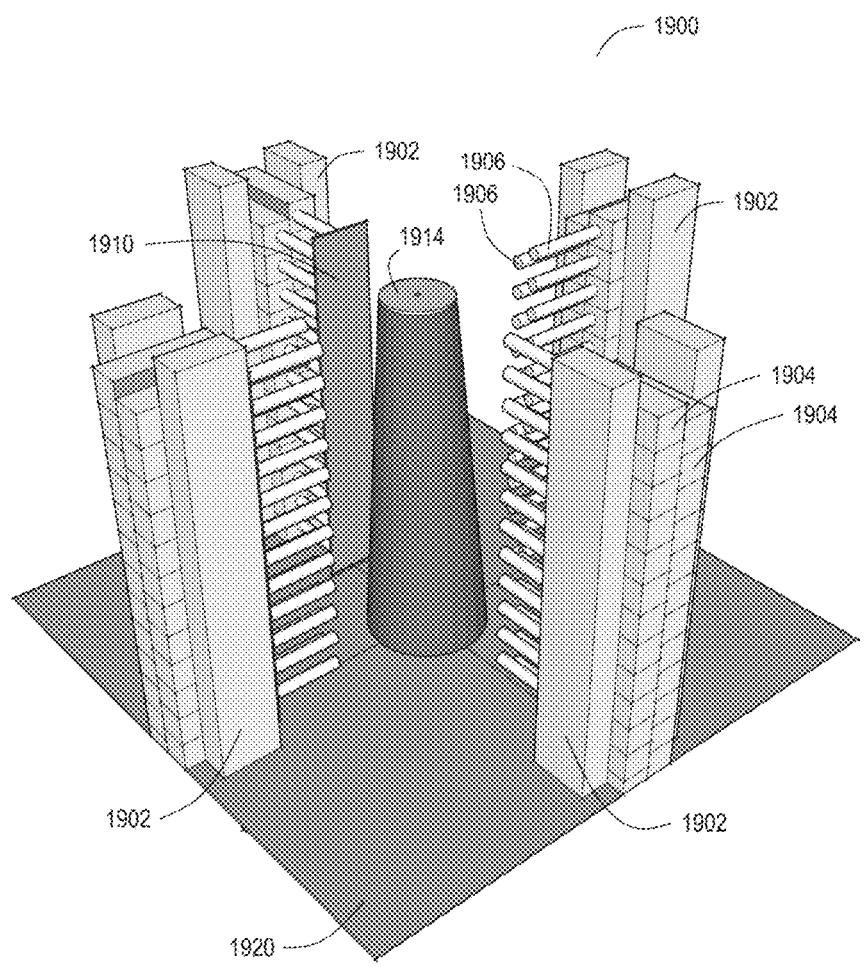
FIGS. 19A-19F show various views of an embodiment of an embodiment of a circumferentially operable reconfigurable pin tool apparatus of Type B, with actuated rods extending inward from a set of peripheral towers.
Figure 19B:
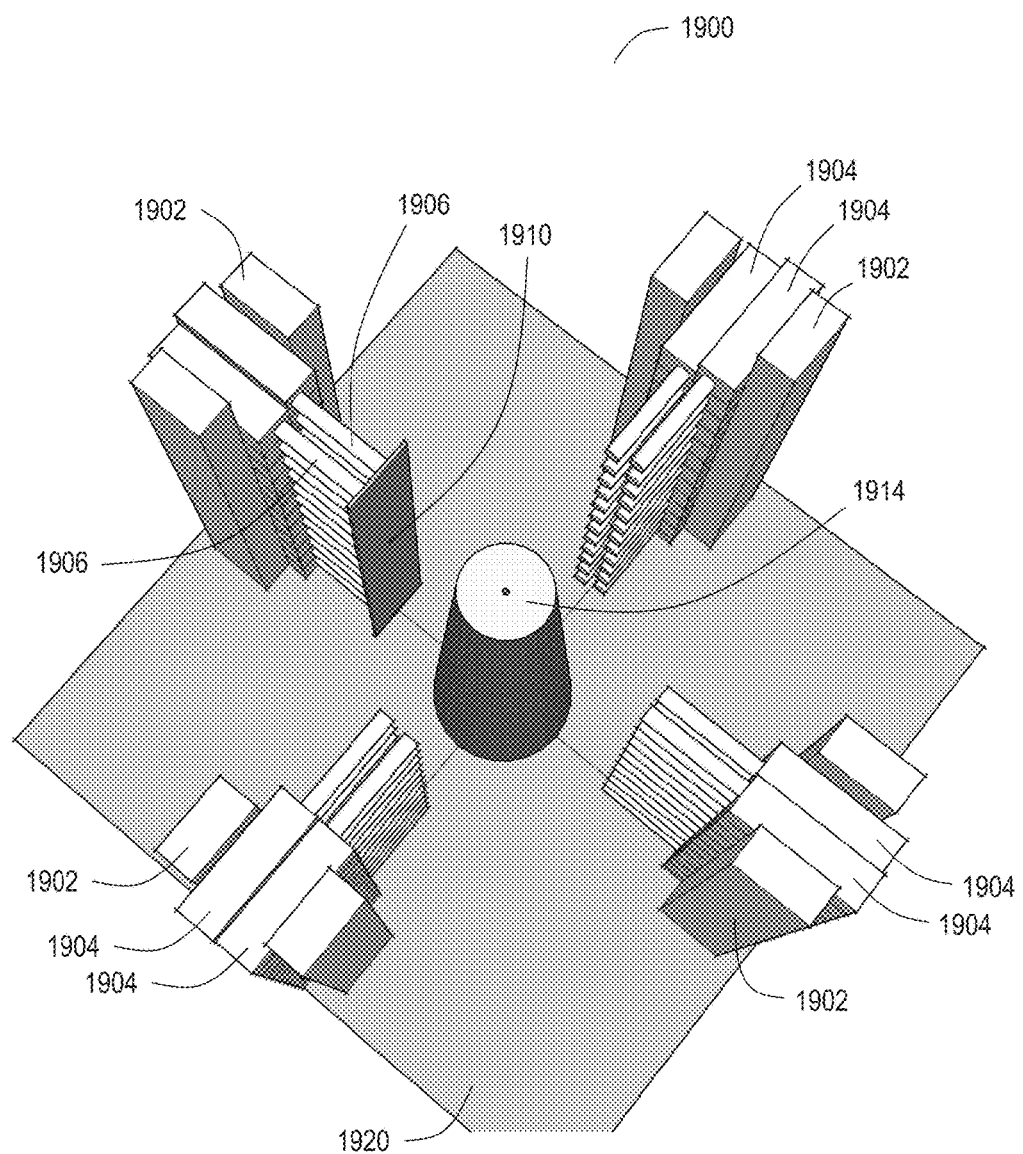
Figure 19C:
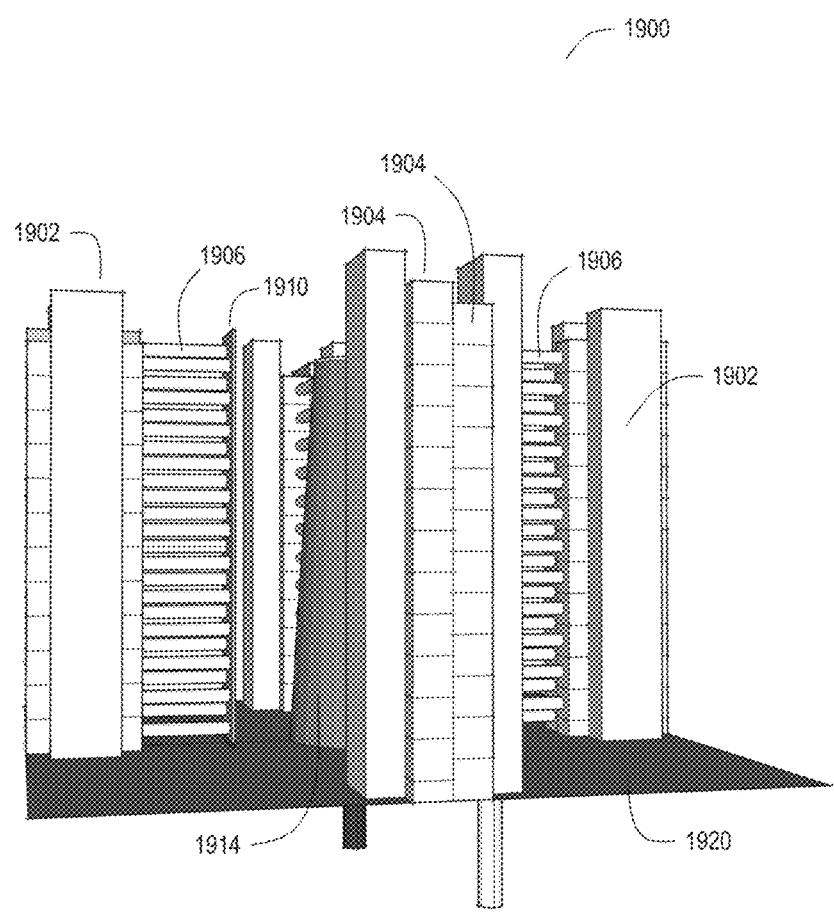

FIGS. 19A-19F show various views of an embodiment of a circumferentially operable reconfigurable pin tool apparatus 1900 of Type B, with actuated rods 1906 extending inward from a set of peripheral actuator towers 1902 toward a centrally-positioned inflatable positive molding dummy 1914. FIG. 19A shows an isometric view the circumferentially operable reconfigurable pin tool apparatus 1900; FIG. 19B shows a steep top down perspective view of the same embodiment; and FIG. 19C shows a side view of the same embodiment. This circumferentially operable reconfigurable pin tool 1900 has four peripheral actuator towers 1902 positioned at the vertices of a square pattern around central positive molding dummy 1914, all arranged on a base plate 1920. The peripheral actuator towers 1902 of this particular embodiment have two columns of actuator units, the columns being staggered with respect to each other, such that the actuator units and rods 1906 are not at the same elevation.

The arrangement of actuator units 1904 may vary in a number of ways in various embodiments. For example, rather than two columns of actuator units in each tower 1902, there could be a single column, or three or more columns. Each actuator unit 1904 hosts an actuating rod 1906, typically moved by a small motor (not shown) that can move the rod in (toward a central position) and out (away from the center), under the control of an electronic network and driven by software according to a method such as that described by FIG. 15. The actuator units 1904 within each tower could be parallel to each other instead of being staggered. Further, the number of actuator unit towers 1902 may vary in number and in placement configuration. In some embodiments, there may be three towers 1902 equally spaced apart, or there could be five or more towers 1902. Further, in another embodiment, there may be four towers 1902, but placed in an arrangement other than at the vertices of a square.

Figure 19D:
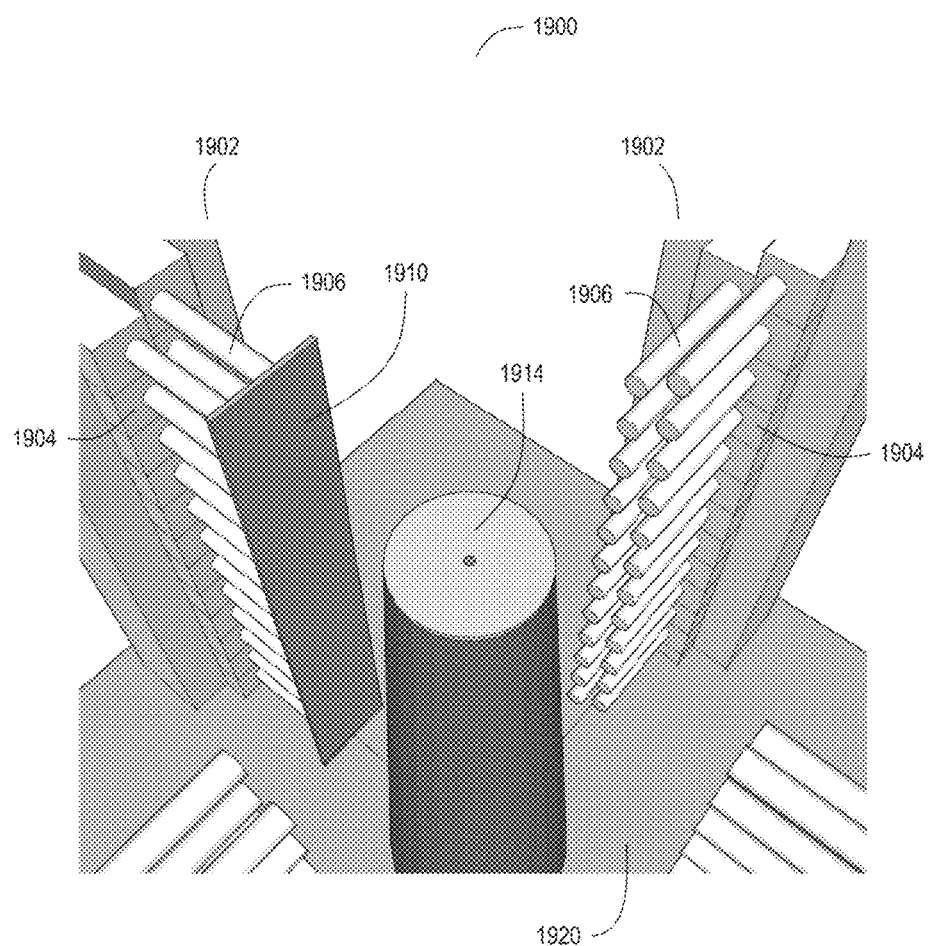

FIG. 19D shows a top perspective view of the circumferentially operable reconfigurable pin tool apparatus 1900 that focuses on an upper portion thereof, showing a centrally positioned inflatable rubber cone 1914 that acts a molding dummy, and a metal plate disposed along the internal ends of an array of inwardly directed pins 1906.

Figure 19E:
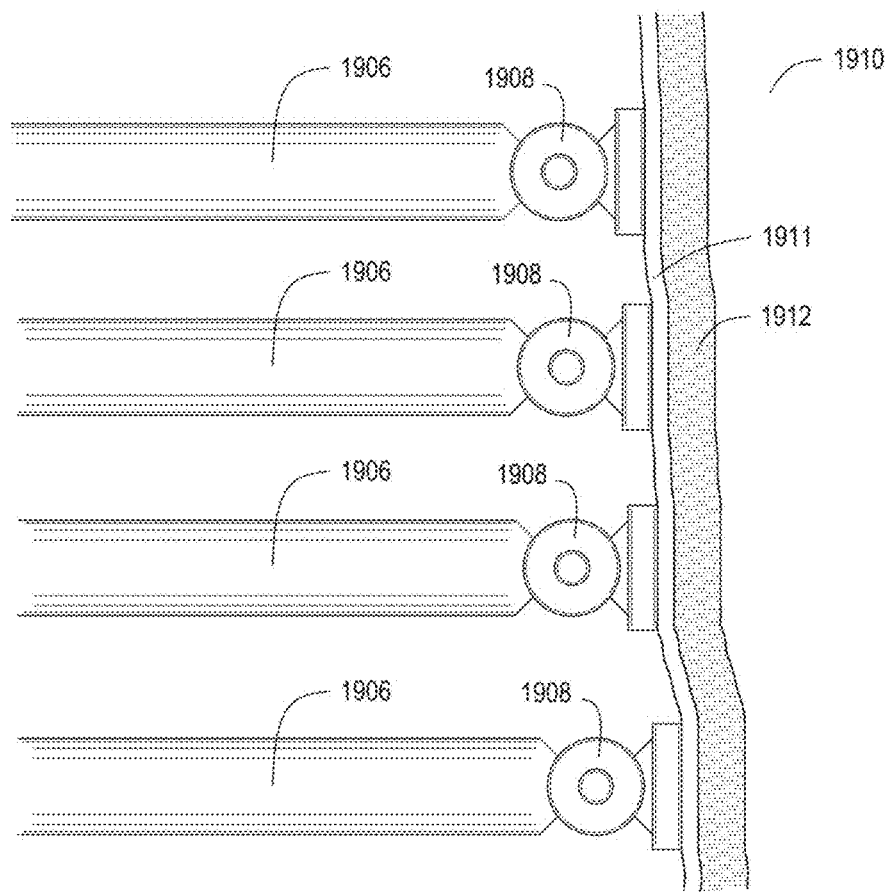

FIG. 19E shows details of this arrangement: the internal ends of inwardly directed pins 1906 have been fitted with gimbal-enabled plates within a clevis type of connection 1908. Gimbaled plates 1908 are shown engaging an embodiment of a compliant molding surface 1910 that is placed to intervene between the internal ends of inwardly directed pins 1906 and the site of engagement against an external surface of a target article (not shown) that is arranged around central positive molding dummy 1914. This particular compliant molding surface includes a sheet metal layer 1911 and a foam layer 1912. The function of compliant molding surface 1914 is to create a smooth molding surface to press against the target article. In some instances, absent such a curve smoothing device, unwanted segmentation may be created on the surface of the target article from the internal ends of inwardly directed rods, with or without attached plates. (An analogous smooth curving device can also be applied for use with circumferential reconfigurable devices of Type A, as shown in FIGS. 18A-18C.)

Figure 19F:
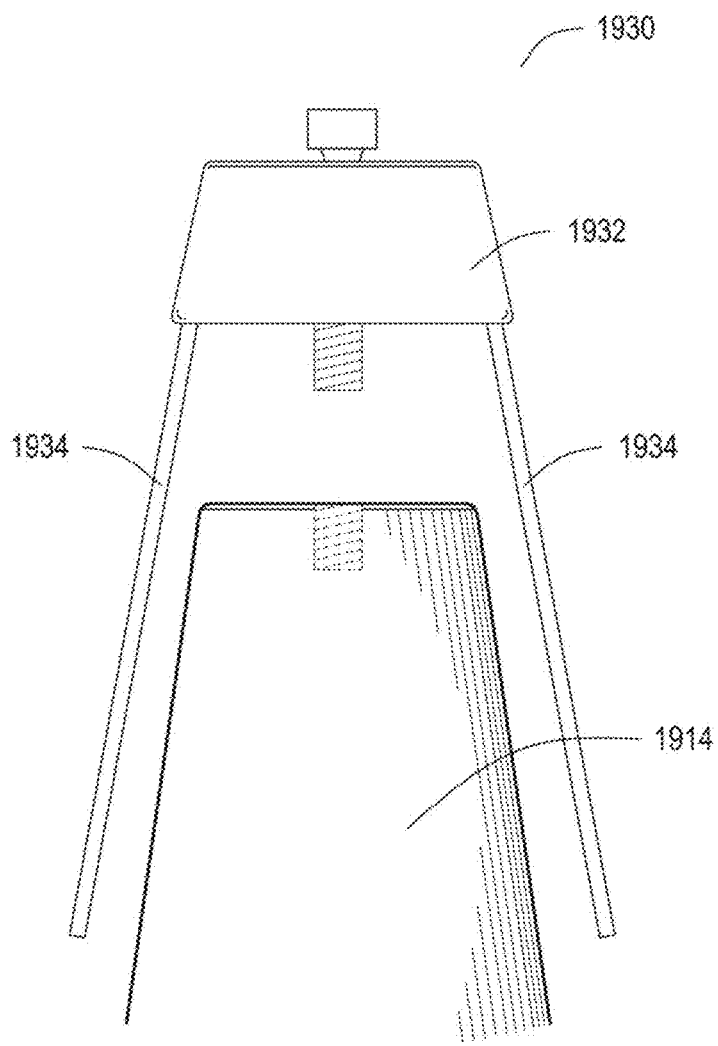

FIG. 19F shows a side view of an embodiment of an target article positioned over a central inflatable positive molding dummy 1914, in the context of the arrangement shown in FIG. 19D. This particular target article is shown as a modular prosthetic socket (as referenced above) placed upside down over molding dummy 1914, such that each strut being thermally reformed would be placed directly over a column of actuatable pins. As pins 1906 are actuated to move inward, they encounter the external surface of a warm and malleable strut (not shown). As pins 1906 move further inward and arrange themselves in a final contour directed by software that replicates contours of a residual limb, the struts assume those same body contour profiles, as they are pressed into the compliant but resistive surface of centrally positioned molding dummy 1914. When the thermally reformed struts have cooled enough that they retain their reformed shape, rods 1906 are withdrawn back toward the peripheral actuator towers, and the newly reshaped prosthetic socket, with four simultaneously reformed struts, can be lifted off the central molding dummy 1914.

FIGS. 20A-35 show a number of embodiments and mechanical features in further detail. These features may be substituted for features described above in the context the embodiments shown in FIGS. 1-6, and 8-11, or added thereto.

Recalling, as described above, that some embodiments of a contour replicating apparatus 1 (as shown in FIGS. 1-6, and 8-11) make use of a pin movement resistance mechanism 70 that involves a variably pressurizable container of silicon in a central section of which the pins are immersed. When the silicon container is not pressurized, the pins can move with relative ease. When the silicon container is pressurized, the pins are stabilized in position sufficiently that they can act as a molding bed. This is but one embodiment of a mechanism that can controllably allow pins to move into position and then be stabilized or locked so they can collectively act as a molding bed.

FIGS. 20A-20D show an alternative mechanism 2000 for allowing pins 2002 to move freely when desired, and to be locked in place when they are in a desired position. FIG. 20A shows a side profile view of a square pin 2002 with slots on two opposing sides. FIG. 20B shows an array of pins arranged as a pin bed 2009 within a series of plates—top and bottom aligning plates 2005 and an offsettable plate 2006—which is shown in FIG. 20C. Aligning plates 2005 have square or rectangular holes that allow free through-movement of slotted pins 2002. Offset plate 2006 has through holes that are substantially identical to those of alignment plates 2005, except for a narrower expanded portion of the hole on one of the four sides of the rectangular hole.

FIG. 20D addresses the role of offsettable plate 2006 in stabilizing pins 2002. After pins 2002 have been placed in the desired position such that the pin bed as a whole replicates the contour of a body part, such as a residual limb, a lever can move the offsettable plate 2006 with respect to the two aligning plates 2005 such that the slots of the slotted pins 2002 are pushed into the narrow adjunct of the offset plate holes. In that position, therefore, the pins 2002 are locked in their desired position. Label 2007 points to the offset of offsettable plate 2006 with respect to its neighboring aligning plate 2005.

Many variations on this type of pin locking mechanism, as well as other types of mechanical locking systems, may be used in alternative embodiments. Any approaches to controlling pins 2002 such that they can move freely when movement is needed, and such that pins 2002 can be locked in position when a stable molding surface has been achieved, may be used in various alternative embodiments.

Contour replicating apparatus 1, as shown in FIGS. 1-6 and FIGS. 8-11, include particular examples of mechanisms that move actuatable pins 340 and that lock them in place, after having been moved. Numerous alternative solutions to these mechanical aspects of the technology can provide appropriate functionalities, and may have particular advantages in alternative embodiments. Some of these alternative solutions are shown in FIGS. 21-29.

FIG. 21 shows an embodiment of a mechanism 2100 for moving a pin 341, in which pin 341 is positioned proximate a screw 343. Rotational movement of screw 343 can drive movement of pin 341 from a neutral position to a desired position. This mechanism can be driven manually or by an automated mechanism. Return of pin 341 to a neutral position may be facilitated by way of gravity or by a spring mechanism.

FIG. 22 shows an embodiment of a mechanism 2200 for moving a pin that is in the form of a screw or threaded rod 344. Rotational movement of screw 344 can drive movement of the pin from a neutral position to a desired position. This mechanism can be driven manually or by an automated mechanism.

Figure 23:
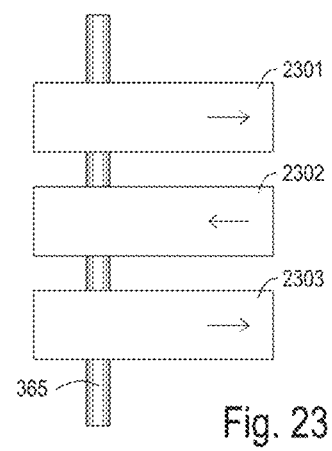
FIG. 23 shows an embodiment of a mechanism that involves three plates through which pin is threaded.

FIG. 23 shows an embodiment of a mechanism 2300 that involves three plates through which a pin 345 is threaded. A friction-offset plate 2302 is positioned between upper alignment plate 2301 and lower alignment plate 2303. Lateral movement of friction offset plate 2302 with respect to upper alignment plate 2301 and lower alignment plate 2303 exerts a frictional stop on the through movement of pin 365. This mechanism is simpler than the mechanism shown in FIG. 20, but the two mechanisms are related in their general principle.

Figure 24:
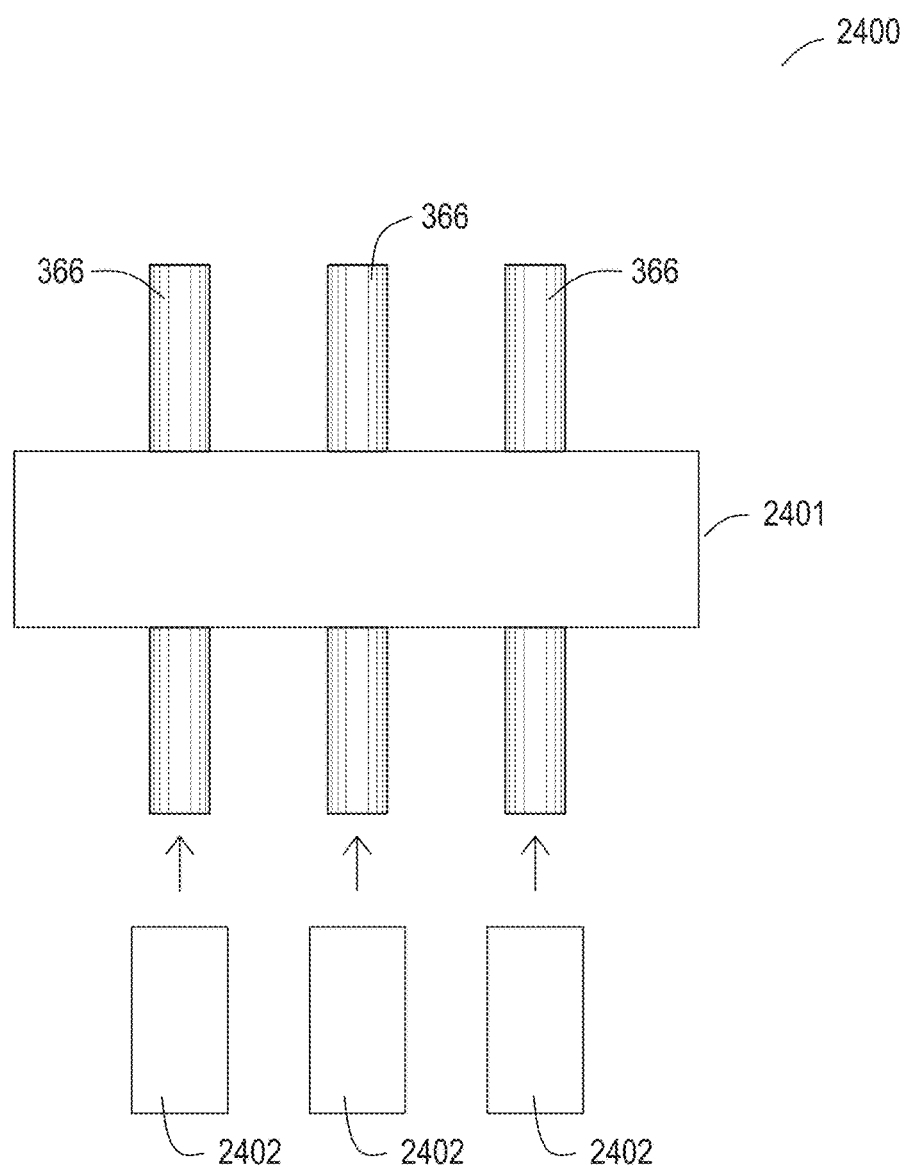
FIG. 24 shows an embodiment of a mechanism in which pins are individually actuated by small motors below each pin.

FIG. 24 shows an embodiment of a mechanism 2400 in which pins 346 are individually actuated by small motors 2402 below each pin, the pins being supported by a pin support platform 2401. This arrangement is one in which the rods or pins 366 are self-actuating, in that they do not require manipulation by a CNC machine to be moved into the desired position.

Figure 25:
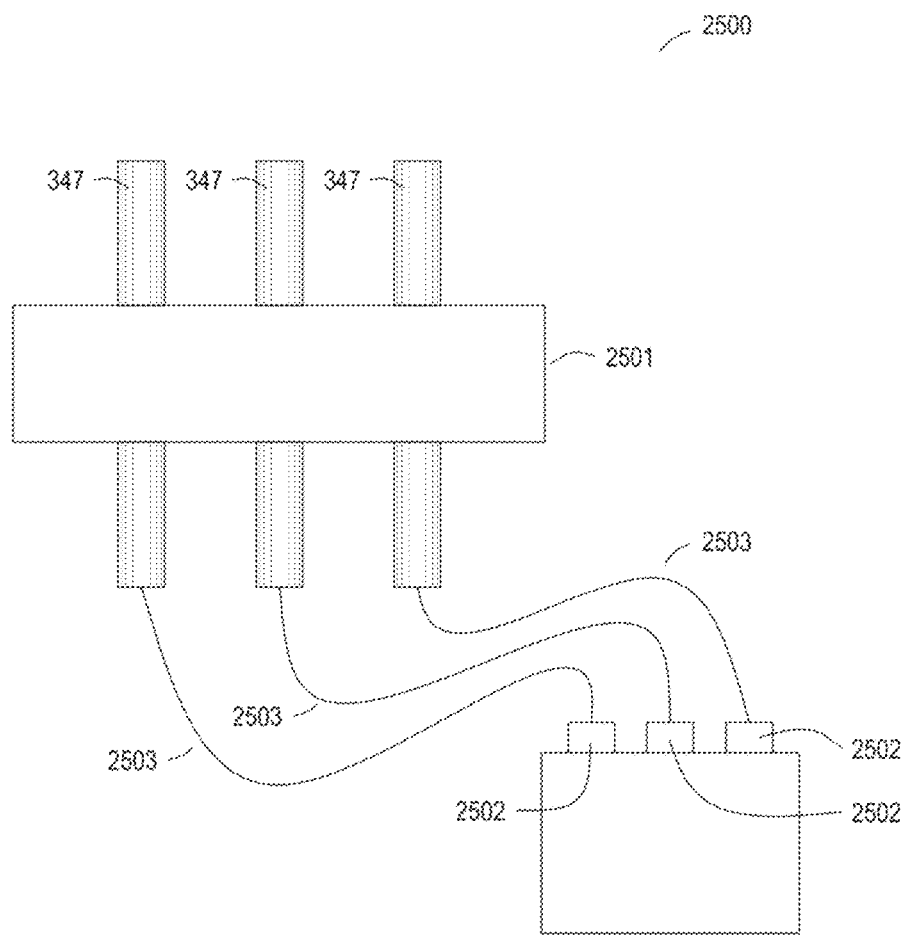
FIG. 25 shows an embodiment of a mechanism in which pins are individually actuated by small motors as an array, the motors being connected to the pins via cables.

FIG. 25 shows an embodiment of a mechanism 2500 in which pins 347 are individually actuated by small motors 2502 in an array, the motors 2502 and pins 347 being connected by cables 2503, and the pins 347 being supported by pin support platform 2501. This is also an arrangement in which rods or pins 347 are self-actuating. This mechanism 2500 (in contrast mechanism 2400 of FIG. 24) has greater spatial latitude in terms of configurations. The small motors 2502 do not need to line up directly behind the pins 347 they actuate, they can be wider than the pins 347, and they can be consolidated into a spatially convenient location.

Figures 26A, 26B:
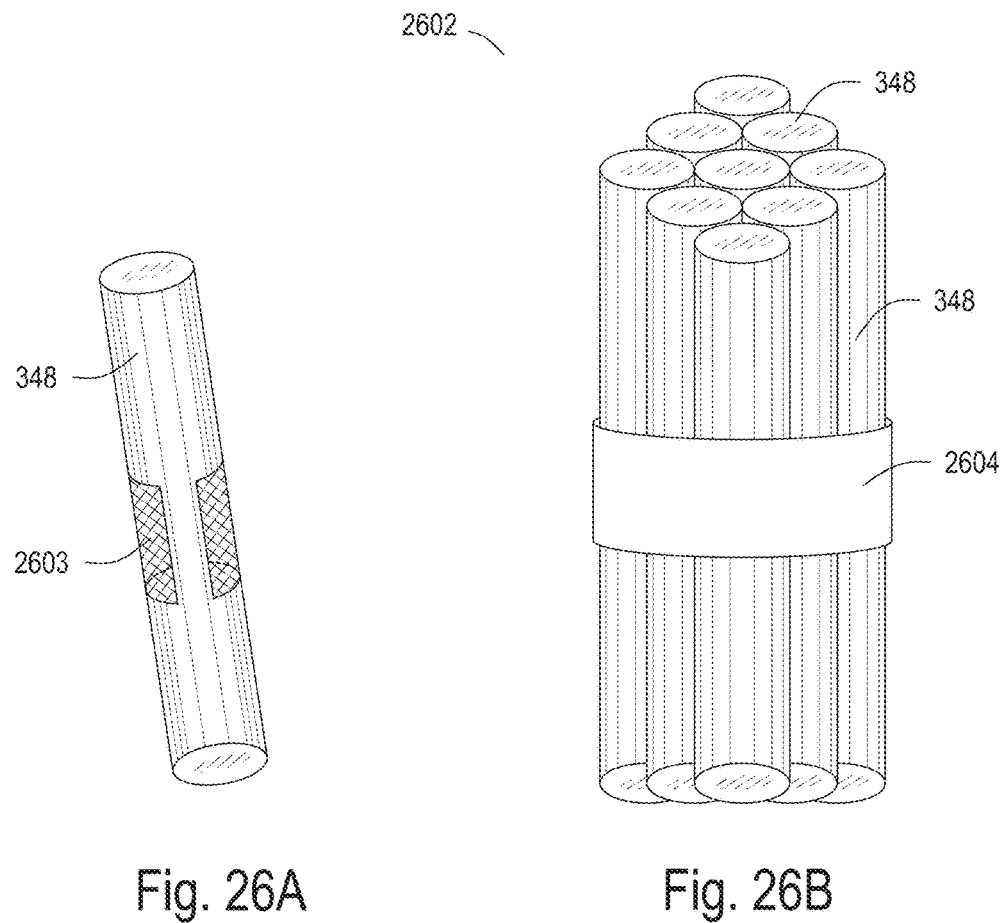
FIG. 26A shows an embodiment of a pin with a friction-enhancing wrap or surface feature that decreases inadvertent slippage with respect to neighboring pins.
FIG. 26B shows an embodiment of pins in which they are clustered as set, and drawn tightly together with a compressing wrap or band that decreases inadvertent slippage of pins with respect to neighboring pins.

FIGS. 26A and 26B show embodiments in which friction between neighboring pins is enhanced to stabilize pins in place. FIG. 26A depicts a pin 348 that may be used in an embodiment in which pins are not self-actuated, but are rather moved en masse by a molding surface, and in which pins 348 are stabilized, at least in part, by the closeness of their packing. In this circumstance, pin packing may not be perfect, and as gaps develop around an individual pin 348, it can slip. Accordingly, FIG. 26A shows an embodiment of a pin 348 with a friction-enhancing wrap or surface feature 2603 that decreases inadvertent slippage with respect to neighboring pins.

FIG. 26B shows an embodiment of a pin arrangement 2602 in which pins 348 are clustered as a set and drawn tightly together with a compressing wrap or band 2604 that decreases inadvertent slippage with respect to neighboring pins. In practice, pins 348 could be moved en masse or by individual actuation. After being moved to an appropriate position, pins 348 can be frictionally stabilized against slipping with respect to their neighbor by drawing them closely together or increasing a inwardly directed tension by tightening circumferential wrap or band 2604.

Figure 27:
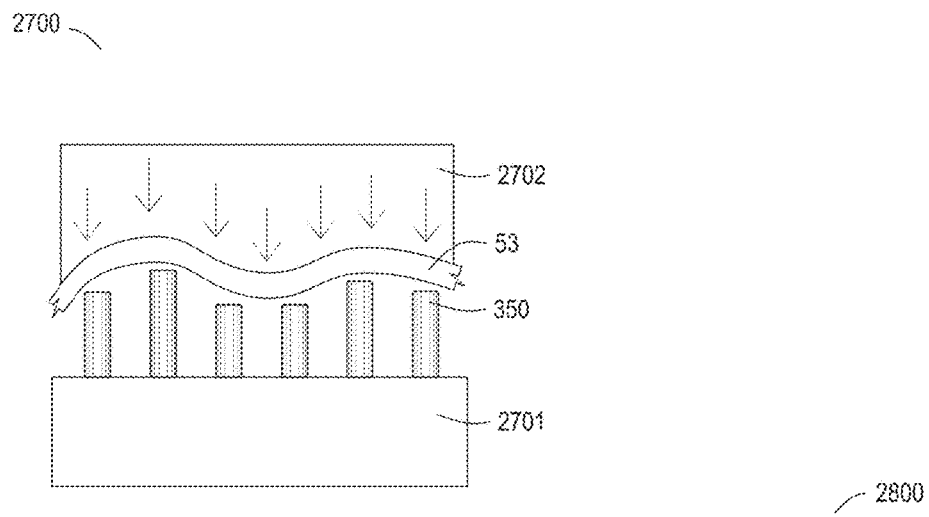
FIG. 27 shows an embodiment of a mechanism in which a fluid bladder applies pressure against a reconfigurable pin bed that forms a molding surface.
Figure 28:
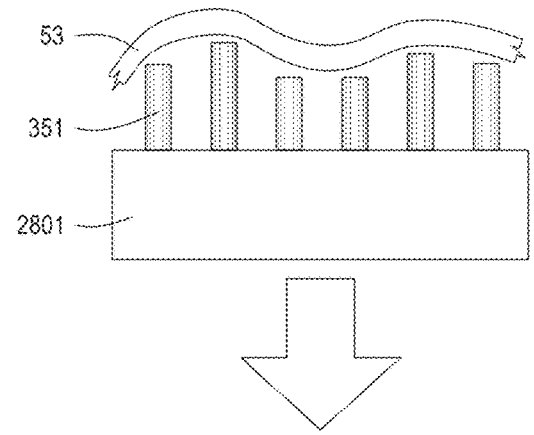
FIG. 28 shows an embodiment of a mechanism in which a vacuum form is arranged over a reconfigurable pin bed that forms a molding surface.
Figure 29:
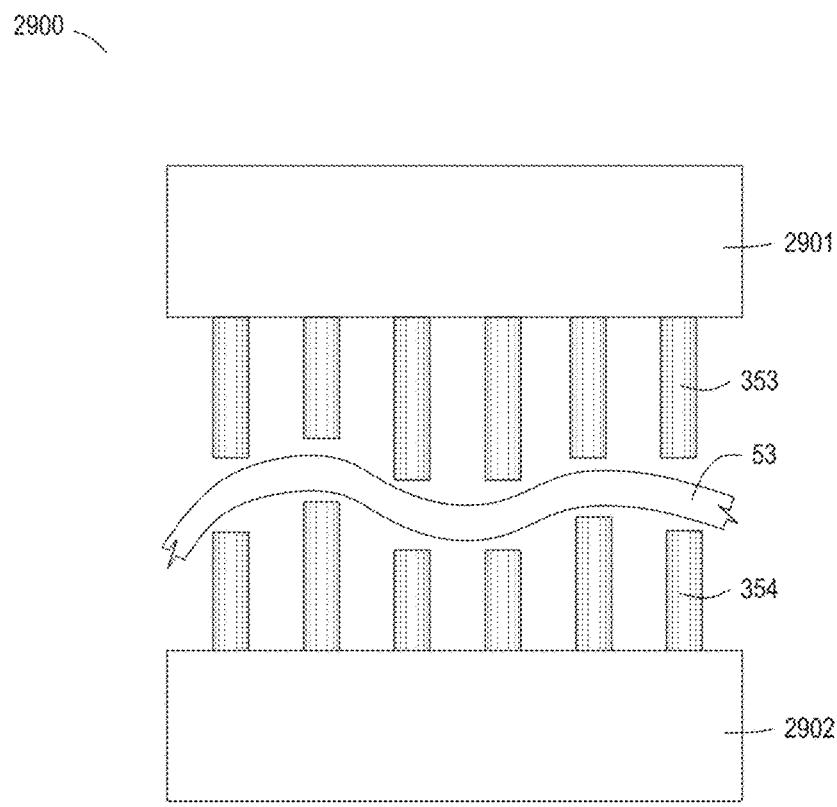

Pressure may be applied to a compliant thermoplastic article so as to reform it into a desired shape by various mechanisms, several of which are illustrated in FIGS. 27-29. FIG. 27 shows an embodiment of a mechanism 2700 in which a fluid bladder applies pressure against a reconfigurable pin bed that forms a molding surface. This mechanism represents, in a schematic way, the mechanism shown in detail in FIGS. 1-6 and 8-11. Pins 350 or supported by platform 2701. In this arrangement, a well-supported compliant or adaptive fluid bladder 2701 is inflated and expands toward (as indicated by arrows) a reconfigurable surface defined by pins 350. A compliant target thermoplastic article 53 is positioned between the encroaching bladder 2702 and the pin bed. As the surface of expanding inflatable bladder 2701 engages the surface of pins 350, article 53 is pressed into the configuration as defined by the pins.

FIG. 28 shows an embodiment of a mechanism 2800 in which a vacuum form is arranged over a reconfigurable pin bed (as defined by pins 351) that forms a molding surface. Pins 351 are supported by support platform 2801, and compliant target thermoplastic article 53 is positioned over the pins. If necessary, an airtight seal is placed over the article, and then a vacuum form is placed around the pins and support platform, and a vacuum drawn as indicated by the arrow. As the space surrounding the pins and platform is evacuated, article 53 is pressed into the configuration as defined by the pins.

FIG. 29 shows an embodiment of a mechanism 2900 in which two opposing sets of pins, compress a target compliant thermoplastic article position between them. Upper support platform 2901 supports pins 353, and lower support platform 2902 supports pins 354. In general, the molding surfaces defined by upper pins 353 and lower pins 354 are complementary, but they do not need to be exactly complementary. By subtle variations in the opposing pin beds, as target article 53 is pressed into a desired form, the thickness of the reformed article 53 can vary in a controlled manner.

Pins included in embodiments of a reconfigurable pin tool may have various cross sectional profiles and be arranged in various packing patterns and densities. FIG. 30A shows an array of pins having a round cross sectional profile. FIG. 30B shows an array of pins having a hexagonal cross sectional profile. FIG. 30C shows an array of pins having a square cross sectional profile. In other variations, the pins may be spaced apart and have larger surface area heads or facets that fill or substantially fill the area in a reconfigurable or actuatable surface. These various profiles and packing arrangements are merely representative of many that are available and may be selected based on their relative advantages and disadvantages.

Figure 31:
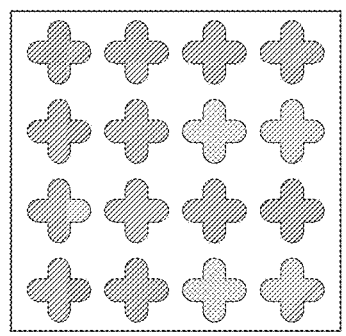
FIG. 31 shows a pin shape that can be placed on the engaging surface of a pin that can then be used to impart a particular pattern onto material being molded.

FIG. 31 shows an example of a particular pin shape that can be placed on the upper surface of a pin with any cross sectional shape, which then can be used to impart a unique pattern onto material being formed.

FIG. 32 shows an embodiment 3200 of a pin 355 in which a hexagonal engaging element 3203 is attached to the molding engagement end of a pin 355 by way of a gimbal 3202. This arrangement allows an engaging surface of the pin to align tangentially against the surface of an article being molded or reformed regardless of the angle of curvature of the article at the point of engagement.

Figure 33:
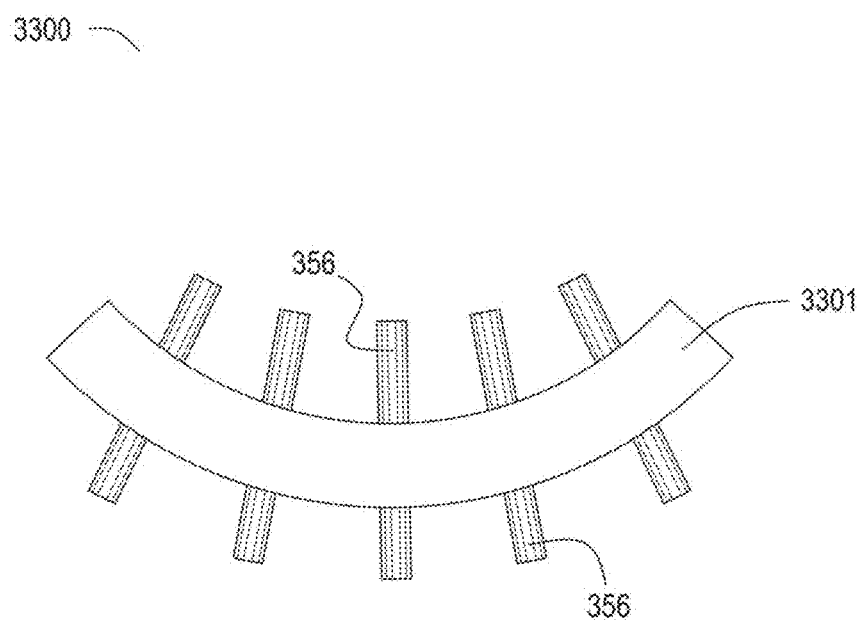
FIG. 33 shows a pin field being supported by a contoured pin support platform.

FIG. 33 shows an embodiment a contour replicating apparatus 3300 in which a support platform 3300 forms a shaped pin field. Various embodiments of reconfigurable pin tools and molding rigs have been described above in which a pin field is hosted within a platform having supporting plates and actuatable plates, and these embodiments are typically shown as having a flat pin support platform. From such a flat support platform, pins can stage a contoured surface, but in some instances the elevational changes in the contour may be limited by the flatness of a support platform. According, embodiments of the invention include those that have a contoured platform, such as pin support platform 3301, hosting pins 356. Pins, such as pins 356 typically include an end that contributes to a molding surface (an engagement end) and a back end. As drawn, pin support platform 3301 could represent either a convex or a concave molding surface, either surface being formed by the engagement ends of pins 356.

Figure 34:
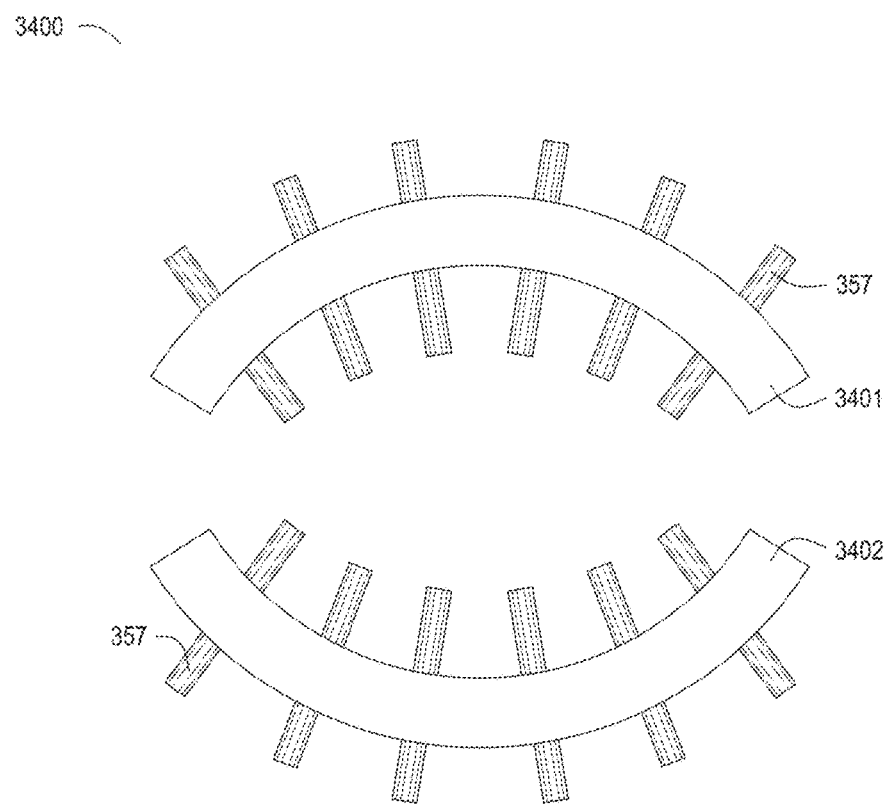
FIG. 34 shows two contoured pin support platforms working together as an integrated molding surface.

FIG. 34 shows an embodiment a contour replicating apparatus 3400 in which has two support platforms 3401 and 402 that collectively form a complex or integrated molding surface. As noted above in the context of describing embodiment 3300 (FIG. 33), embodiment 3400 could represent a molding surface engaging as a positive mold, moving pins externally to engage as a molding surface, or embodiment 3400 could represent a molding surface engaging as a negative mold, moving pins internally to engage as a molding surface.

Any one or more features of any embodiment of the invention, device or method, can be combined with any one or more other features of any other embodiment of the invention, without departing from the scope of the invention. Therefore, the invention is not limited to the embodiments that are described or depicted herein for purposes of exemplification, but is to be defined only by a fair reading of claims appended to the patent application, including the full range of equivalency to which each element thereof is entitled. Further, while some theoretical considerations have been offered to provide an understanding of the technology (as understood by the inventors), such as the effect of pressure within an embodiment of a pin movement resistance mechanism, the claims are not bound by such theory.

What is claimed is:

1. A method of reforming a thermoplastic article to assume a desired shape, the method comprising:
heating a thermoplastic article to render it malleable;
providing a field of longitudinally extending pins, each pin having an end facet at one end of the pin, the pins extending parallel to each other, the pins being relatively longitudinally positionable relative to one another;
relatively positioning the pins in the field so that end facets corresponding to at least a portion of the field of pins define a molding surface that conforms to the desired shape;

after relatively positioning the pins, pressing via a pressurized medium the malleable thermoplastic article against the pins in the field
to reform at least a portion of the thermoplastic article into the desired shape; and
separating the reformed thermoplastic article from the molding surface, wherein the reformed thermoplastic article retains the desired shape after separating from the molding surface.

2. The method of claim 1, wherein the thermoplastic article comprises at least a portion of a medical device.

3. The method of claim 1, wherein the thermoplastic article comprises a component of a prosthetic device.

4. The method of claim 1, wherein the thermoplastic article comprises a strut for a prosthetic socket.

5. The method of claim 1, wherein the body part comprises a residual limb.

6. The method of claim 1, wherein the thermoplastic article comprises a thermoplastic-fiber composite.

7. The method of claim 6, wherein the fiber of the thermoplastic-fiber composite comprises multiple continuous fibers.

8. The method of claim 1, further comprising, prior to the removing step, allowing the thermoplastic article to cool sufficiently, such that the thermoplastic article retains the desired shape.

9. The method of claim 1, further comprising, before the placing step:
acquiring digital data representing a portion of a body part; and
using the digital data to relatively position the pins so that the end facets corresponding to the least one portion of the field of pins define the molding surface that replicates the body part.

10. The method of claim 9, wherein using the digital data comprises using a CNC machine to adjust positions of the pins.

11. The method of claim 9, wherein using the digital data comprises moving the pins individually using a motor.

12. The method of claim 1, wherein the desired shape replicates a portion of a body part.

13. The method of claim 1, wherein a motor is used to move the pins.

14. A method of reforming a thermoplastic article to assume a desired shape, the method comprising:
providing positionable pins having end facets, the end facets defining a molding surface;
heating a thermoplastic article to render it malleable;
acquiring digital data representing a portion of a body part;
using the digital data to relatively position the pins so that the molding surface defined by the end facets conforms to the desired shape that replicates the body part, wherein the pins are relatively positioned by using a CNC machine to adjust positions of the pins based on the digital data;
after relatively positioning the pins, pressing via a pressurized medium the malleable thermoplastic article against the pins
to reform at least a portion of the thermoplastic article into the desired shape; and
separating the reformed thermoplastic article from the molding surface, wherein the reformed thermoplastic article retains the desired shape after separating from the molding surface.

15. A method of reforming a thermoplastic article to assume a desired shape, the method comprising:
providing a molding surface that is reconfigurable with a motor;
heating a thermoplastic article to render it malleable;
acquiring digital data representing a portion of a part;
using the digital data to operate the motor to configure the molding surface into the desired shape;
after configuring the molding surface, pressing via a pressurized medium the malleable thermoplastic article against the molding surface
to reform at least a portion of the thermoplastic article into the desired shape; and
separating the reformed thermoplastic article from the molding surface, wherein the reformed thermoplastic article retains the desired shape after separation from the molding surface.

16. The method of claim 15, wherein the molding surface comprises positionable pins, and the motor moves the pins.

17. The method of claim 16, wherein the molding surface comprises end facets of the pins.

18. The method of claim 15, wherein the part is a human body part.

* * * * *